(12) United States Patent
Redda et al.

(10) Patent No.: US 11,839,609 B1
(45) Date of Patent: Dec. 12, 2023

(54) SUBSTITUTED TETRAHYDROISOQUINOLINES AS ANTI-MITOTIC DRUG IN TRIPLE NEGATIVE BREAST CANCER

(71) Applicant: Florida A&M University, Tallahassee, FL (US)

(72) Inventors: Kinfe Ken Redda, Tallahassee, FL (US); Karam F. A. Soliman, Tallahassee, FL (US); Madhavi Gangapuram, Tallahassee, FL (US); Elizabeth Mazzio, Quincy, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 17/745,924

(22) Filed: May 17, 2022

Related U.S. Application Data

(60) Provisional application No. 63/189,475, filed on May 17, 2021.

(51) Int. Cl.
*A61K 31/472* (2006.01)
*A61P 35/00* (2006.01)

(52) U.S. Cl.
CPC ............ *A61K 31/472* (2013.01); *A61P 35/00* (2018.01)

(58) Field of Classification Search
CPC .................................................. A61K 31/472
See application file for complete search history.

(56) References Cited

U.S. PATENT DOCUMENTS

| | | | | |
|---|---|---|---|---|
| 8,889,713 B1 * | 11/2014 | Redda | ................... | C07D 217/08 514/310 |
| 2019/0100495 A1 * | 4/2019 | Redda | ................... | C07D 217/08 |

OTHER PUBLICATIONS

Redda et al. Anticancer Research (2016), 36(10), 5043-5052.*
Pindedo et al.( 2000).*
McMahon et al. (2000).*
Gangapuram, M. et al. Substituted Tetrahydroisoquinolines as Microtubule-destabilizing Agents in Triple Negative Human Breast Cancer Cells. Anticancer Res 2016;36(10):5043-52.
Eyunni, Svk et al. J Cancer Sci Ther. 2017, 9(7): 528-540.
Gangapuram, M. et al. Transcriptome Profile Analysis of Triple-Negative Breast Cancer Cells in Response to a Novel Cytostatic Tetrahydroisoquinoline Compared to Paclitaxel. Int J Mol Sci. Jul. 19, 2021; 22(14).
Tamura, Y. et al. A novel method for heteroaromatic N-amines. J. Org Chem. 1972, 40:4133-4135.
Mukopadhyay, C. et al. Distinct effects of EGFR ligands on human mammary epithelial cell differentiation. PLoS One 2013;8(10):e75907.
Olsen, D.A. et al. Increased concentrations of growth factors and activation of the EGFR system in breast cancer. Clin Chem Lab Med 2012;50(10):1809-18.
Peterson, E.A. et al. Amphiregulin Is a Critical Downstream Effector of Estrogen Signaling in ERalpha-Positive Breast Cancer. Cancer Res 2015;75(22):4830-8.
Schmucker, H. et al. Amphiregulin regulates proliferation and migration of HER2-positive breast cancer cells. Cell Oncol (Dordr) 2018;41 (2):159-68.
Williams, C.B. et al. Perspectives on Epidermal Growth Factor Receptor Regulation in Triple-Negative Breast Cancer: Ligand-Mediated Mechanisms of Receptor Regulation and Potential for Clinical Targeting. Adv Cancer Res 2015;127:253-81.
Xiang, G. et al. Prognostic role of Amphiregulin and the correlation with androgen receptor in invasive breast cancer. Pathol Res Pract 2019;215(6):152414.
Higginbotham, J.N. et al. Amphiregulin exosomes increase cancer cell invasion. Curr Biol 2011 ;21 (9):779-86.
Roskoski, R. Jr. The ErbB/HER family of protein-tyrosine kinases and cancer. Pharmacol Res 2014;79:34-74.
Tanaka, H. et al. Nuclear envelope-localized EGF family protein amphiregulin activates breast cancer cell migration in an EGF-like domain independent manner. Biochem Biophys Res Commun 2012;420(4):721-6.
Rego, S.L. et al. Tumor necrosis factor-alpha-converting enzyme activities and tumor-associated macrophages in breast cancer. Immunol Res Jan. 2014;58(1 ):87-100.
Taverna, S. et al. Amphiregulin contained in NSCLC-exosomes induces osteoclast differentiation through the activation of EGFR pathway. Sci Rep 2017;7(1):3170.
Kim, J.W. et al. Amphiregulin confers trastuzumab resistance via AKT and ERK activation in HER2-positive breast cancer. J Cancer Res Clin Oncol 2016;142(1):157-65.
Revillion, F. et al. ErbB/HER ligands in human breast cancer, and relationships with their receptors, the bio-pathological features and prognosis. Ann Oncol 2008;19(1):73-80.
Nickerson, N.K. et al. Autocrine-derived epidermal growth factor receptor ligands contribute to recruitment of tumor-associated macrophage and growth of basal breast cancer cells in vivo. Oncol Res 2013;20(7):303-17.
He, M. et al. The miR-186-3p/EREG axis orchestrates tamoxifen resistance and aerobic glycolysis in breast cancer cells. Oncogene 2019;38(28):5551-65.
Vlaicu, P. et al. Monocytes/macrophages support mammary tumor invasivity by co-secreting lineage-specific EGFR ligands and a STAT3 activator. BMC Cancer 2013;13:197.
Shrivastava, R. et al. M2 polarization of macrophages by Oncostatin Min hypoxic tumor microenvironment is mediated by mTORC2 and promotes tumor growth and metastasis. Cytokine 2019;118:130-43.

(Continued)

*Primary Examiner* — Paul V Ward
(74) *Attorney, Agent, or Firm* — Michele L. Lawson; Smith & Hopen, P.A.

(57) ABSTRACT

Novel compositions and methods of using the compositions to treat triple negative breast cancer are presented. 4-Ethyl-N-(7-hydroxy-3,4-dihydroisoquinolin-2(1H)-yl) benzamide has been shown to downregulate the expression of several genes associated with TNBC such as amphiregulin (AREG), epiregulin (EREG), inhibitor of DNA binding 1 (ID1), inhibitor of DNA binding 3 (ID3), killer cell lectin like receptor C3 (KLRC3), cyclooxygenase-2 (COX2), and intercellular adhesion molecule 1 (ICAM-1). In addition, the compound has been shown to downregulate the oncostatin M(OSM) signaling pathway.

16 Claims, 19 Drawing Sheets

(56) References Cited

OTHER PUBLICATIONS

Tripathi, C. et al. Macrophages are recruited to hypoxic tumor areas and acquire a pro-angiogenic M2-polarized phenotype via hypoxic cancer cell derived cytokines Oncostatin M and Eotaxin. Oncotarget 2014;5(14):5350-68.

Masjedi, A. et al. A mysterious cytokine in cancers. Int Immunopharmacol 2020:107158.

Tawara, K. et al. OSM potentiates pre-intravasation events, increases CTC counts, and promotes breast cancer metastasis to the lung. Breast Cancer Res 2018;20(1):53.

Omokehinde, T. et al. GP130 Cytokines in Breast Cancer and Bone. Cancers (Basel) 2020;12(2).

Doherty, M.R. et al. The opposing effects of interferon-beta and oncostatin-M as regulators of cancer stem cell plasticity in triple-negative breast cancer. Breast Cancer Res 2019;21(1):54.

Junk, D.J. et al. Oncostatin M promotes cancer cell plasticity through cooperative STAT3-SMAD3 signaling. Oncogene 2017;36(28):4001-13.

Bryson, B.L. et al. STAT3-mediated SMAD3 activation underlies Oncostatin M-induced Senescence. Cell Cycle 2017;16(4):319-34.

Litherland, G.J. et al. Protein kinase C isoforms zeta and iota mediate collagenase expression and cartilage destruction via STAT3- and ERK-dependent c-fos induction. J Biol Chem 2010;285(29):22414-25.

Parashar, D. et al. miRNA551 b-3p Activates an Oncostatin Signaling Module for the Progression of Triple-Negative Breast Cancer. Cell Rep 2019;29(13):4389-406.

Cheray, M. et al. KLRC3, a Natural Killer receptor gene, is a key factor involved in glioblastoma tumourigenesis and aggressiveness. J Cell Mol Med 2017;21(2):244-53.

Park, H. et al. Adenylosuccinate lyase enhances aggressiveness of endometrial cancer by increasing killer cell lectin-like receptor C3 expression by fumarate. Lab Invest 2018;98(4):449-61.

* cited by examiner

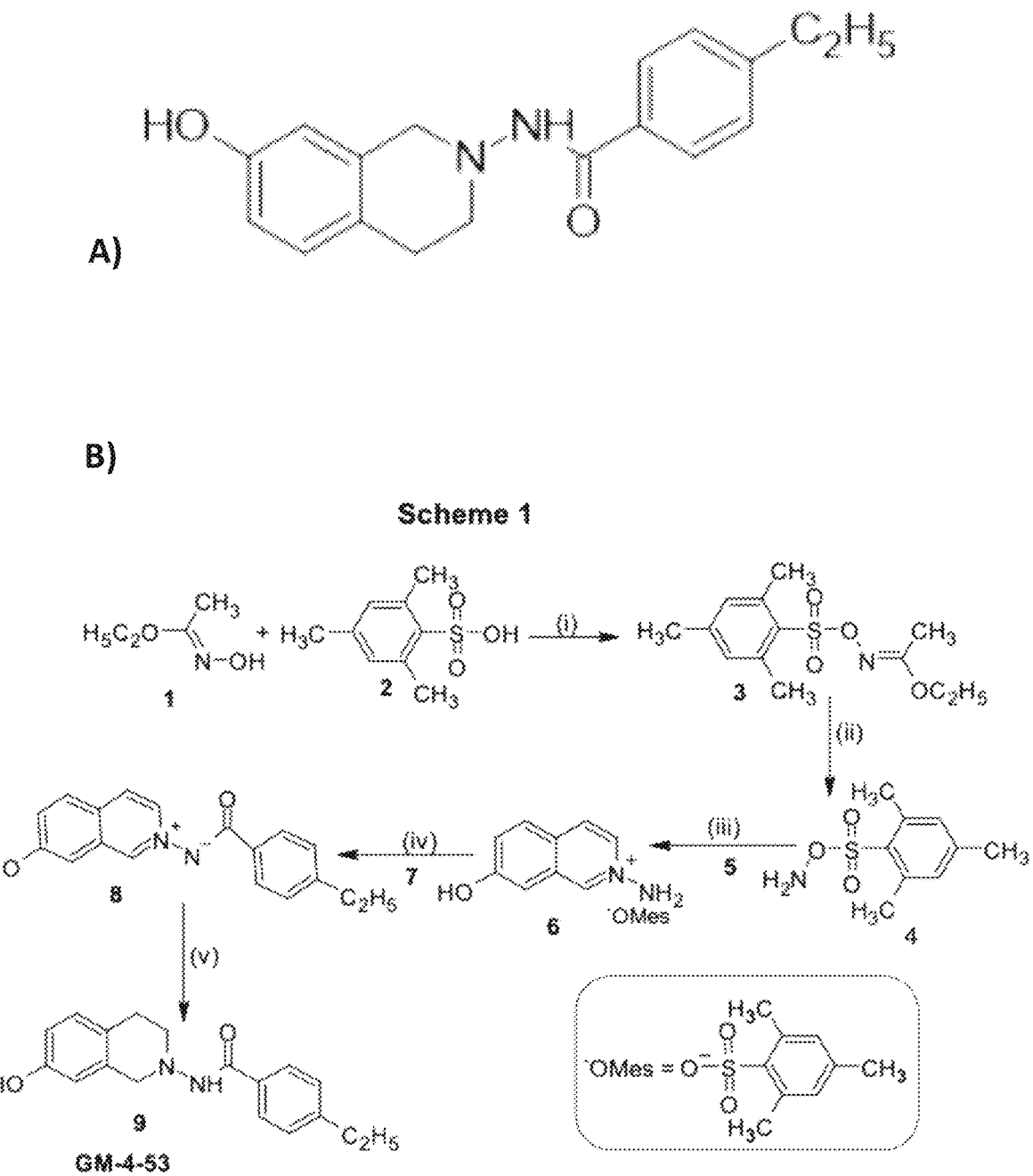
FIG. 1A-B

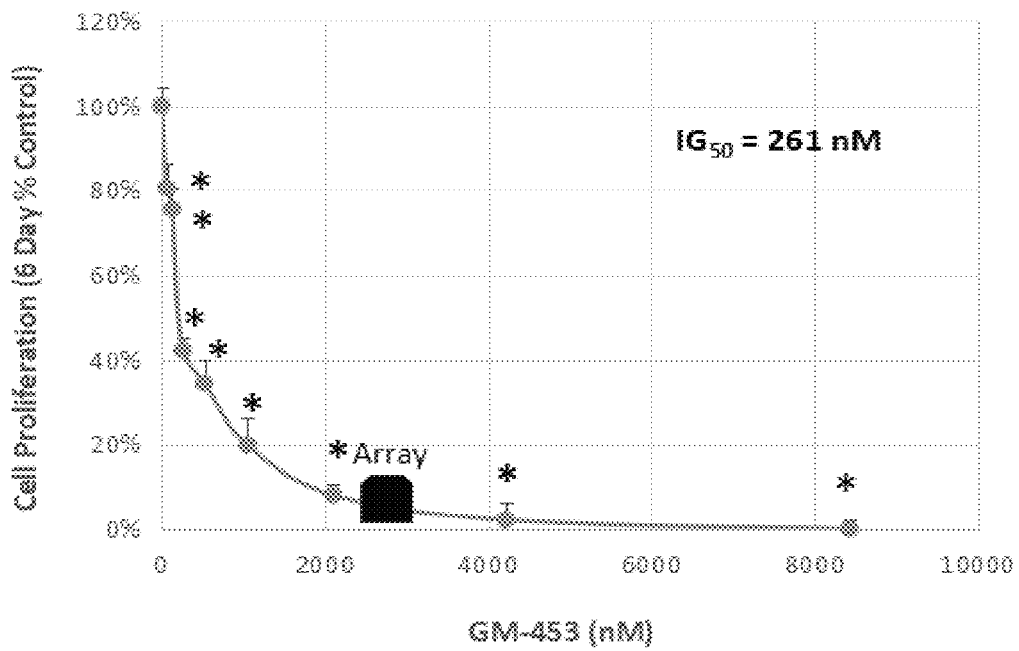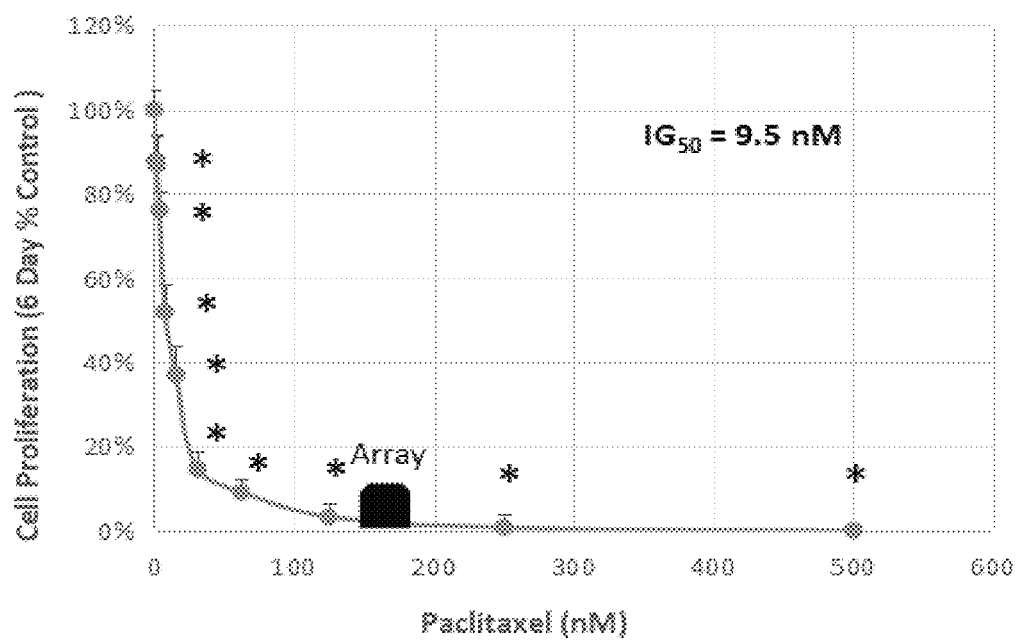
FIG. 2A-B

|  | MCF-7 | Ishikawa | MDA-MB-231 |
|---|---|---|---|
|  | Human Breast Cancer (ER+, PR+) | Human Endometrial Cancer | Human Breast Cancer (TNBC) (ER-) (PR-) |
|  | IC50 (nM) | IC50 (nM) | IC50 (nM) |
| GM-4-53 | 674.01 | 269.61 | 261.26 |

| Gene Symbol | Gene Description | Effects of GM-4-53 (relative to Controls) | | Effects of Paclitaxel (relative to Controls) | |
|---|---|---|---|---|---|
| | | FC | P-Value | FC | P-Value |
| CDCA8 | cell division cycle associated 8 | 2.08 | 8.E-04 | 2.24 | 1.1E-03 |
| CDC20 | cell division cycle 20 | 2.04 | 8.E-03 | 2.32 | 5.8E-03 |
| CSF1 | colony stimulating factor 1 (macrophage) | -3.75 | 4.E-09 | -2.24 | 3.9E-06 |
| CHI3L2 | chitinase 3-like 2 | -2.45 | 2.E-02 | -2.26 | 3.5E-02 |
| OR2M5 | olfactory receptor, family 2, M, 5 | 2.05 | 2.E-02 | 2.07 | 2.3E-02 |
| OR2M3 | olfactory receptor, family 2, M, 3 | 2.20 | 4.E-05 | 3.28 | 3.0E-06 |
| ID3 | inhibitor of DNA binding 3, dominant HLHP | -3.71 | 2.E-07 | -2.10 | 6.0E-04 |
| SNORA55 | small nucleolar RNA, H/ACA box 55 | 2.06 | 7.E-06 | 2.53 | 1.9E-06 |
| MIR3671 | microRNA 3671 | -2.21 | 8.E-04 | -2.74 | 2.0E-04 |
| GBP2 | guanylate binding protein 2, inducible | -2.61 | 4.E-05 | -2.18 | 8.0E-04 |
| COLGALT2 | collagen beta(1-O)galactosyltransferase 2 | -3.17 | 9.E-05 | -2.43 | 3.7E-03 |
| PTGS2 | prostaglandin-endoperoxide synthase 2 | -2.73 | 5.E-03 | -4.12 | 4.0E-04 |
| MIR29B2 | microRNA 29b-2; frame 132 | 2.57 | 2.E-04 | 2.07 | 4.4E-03 |
| ITIH2 | inter-alpha-trypsin inhibitor heavy chain 2 | -2.70 | 2.E-02 | -2.39 | 5.0E-02 |
| TSPAN15 | tetraspanin 15 | -2.32 | 2.E-06 | -2.01 | 3.1E-05 |
| SCD | stearoyl-CoA desaturase | -2.05 | 3.E-06 | -2.13 | 5.9E-06 |
| LOC | uncharacterized LOC100505570 | 2.61 | 9.E-06 | 2.44 | 3.0E-04 |
| SAA1 | serum amyloid A1 | -3.04 | 2.E-03 | -2.50 | 1.9E-02 |
| CD44 | CD44 molecule (Indian blood group) | 2.74 | 4.E-03 | 2.19 | 2.2E-02 |
| DDIAS | DNA damage-induced apoptosis suppressor | 2.01 | 1.E-04 | 2.01 | 3.0E-04 |
| MIR548L | microRNA 548l | 2.76 | 1.E-02 | 2.89 | 9.5E-03 |
| MIRLET7A2 | microRNA let-7a-2 | -2.47 | 4.E-04 | -2.54 | 1.0E-03 |
| TCP11L2 | t-complex 11, testis-specific-like 2 | -2.41 | 2.E-04 | -2.19 | 1.3E-03 |
| KLRC3 | killer cell lectin-like receptor C, 3 | -12.07 | 7.E-07 | -3.21 | 2.6E-03 |
| DUSP6 | dual specificity phosphatase 6 | -2.94 | 1.E-07 | -2.27 | 7.6E-06 |
| SKA3 | spindle and kinetochore associated complex subunit 3 | 2.16 | 9.E-04 | 2.34 | 7.0E-04 |
| ARHGAP11B | Rho GTPase activating protein 11B | 2.30 | 5.E-04 | 3.07 | 1.0E-04 |
| ARHGAP11B | Rho GTPase activating protein 11B | 2.12 | 1.E-02 | 2.05 | 1.2E-02 |
| ARHGAP11A | Rho GTPase activating protein 11A | 2.05 | 3.E-04 | 2.69 | 6.9E-05 |
| KNSTRN | kinetochore-localized astrin/SPAG5 BP | 2.07 | 7.E-05 | 2.58 | 1.5E-05 |
| RPS2 | ribosomal protein S2 | 2.11 | 8.E-05 | 3.11 | 4.3E-06 |
| SHCBP1 | SHC SH2-domain binding protein 1 | 2.12 | 5.E-04 | 2.32 | 6.0E-04 |
| SMG1P7 | SMG1 pseudogene 7 | 2.55 | 1.E-02 | 2.81 | 1.9E-03 |

FIG. 7

| Gene | Description | | | | |
|---|---|---|---|---|---|
| MIR21 | microRNA 21; vacuole MP1 | -2.98 | 3.E-08 | -2.63 | 6.2E-07 |
| SNORD1A | small nucleolar RNA, C/D box 1A; small nucleolar RNA host gene 16 | 2.47 | 2.E-06 | 2.49 | 6.4E-06 |
| JUP | junction plakoglobin | -2.29 | 2.E-03 | -2.02 | 4.8E-03 |
| RAB27B | RAB27B, member RAS oncogene family | -2.14 | 5.E-05 | -2.23 | 3.0E-04 |
| ICAM1 | intercellular adhesion molecule 1 | -3.12 | 1.E-05 | -2.77 | 3.0E-04 |
| ZNF430 | zinc finger protein 430 | 2.26 | 5.E-02 | 2.68 | 2.1E-03 |
| FOSB | FBJ murine osteosarcoma VOH B | -2.59 | 2.E-03 | -2.00 | 2.3E-02 |
| C3 | complement component 3 | -2.73 | 1.E-02 | -2.38 | 4.3E-02 |
| ZNF724P | zinc finger protein 724, pseudogene | 2.30 | 1.E-02 | 3.12 | 3.7E-03 |
| LINC01123 | long intergenic non-protein coding RNA 1123 | -2.66 | 2.E-04 | -2.11 | 7.0E-04 |
| LOC | uncharacterized LOC105373955 | -2.74 | 3.E-06 | -2.46 | 3.7E-05 |
| LOC | uncharacterized LOC105372578 | -2.34 | 5.E-04 | -2.51 | 1.7E-03 |
| ID1 | inhibitor of DNA binding 1, dominant - HLHP | -5.97 | 6.E-11 | -2.24 | 3.3E-06 |
| MIR3193 | microRNA 3193 | -2.19 | 6.E-05 | -2.04 | 3.3E-03 |
| MIR644A | microRNA 644a | 2.22 | 5.E-04 | 2.75 | 3.0E-04 |
| CST2 | cystatin SA | -2.50 | 6.E-04 | -2.21 | 4.5E-03 |
| KIAA1524 | KIAA1524 | 2.03 | 1.E-03 | 2.21 | 1.5E-03 |
| LIPH | lipase, member H | -2.32 | 2.E-05 | -2.28 | 9.0E-05 |
| EREG | epiregulin | -2.84 | 5.E-05 | -3.09 | 2.0E-04 |
| AREG (A) | amphiregulin | -2.72 | 1.E-03 | -2.95 | 1.6E-03 |
| AREG (B) | amphiregulin | -2.41 | 4.E-03 | -2.91 | 2.6E-03 |
| TMEM156 | transmembrane protein 156 | -2.10 | 2.E-02 | -2.40 | 1.3E-02 |
| ATP8A1 | ATPase, (APLT), class I, type 8A, member 1 | -2.63 | 8.E-07 | -2.21 | 5.6E-05 |
| SCLT1 | sodium channel and clathrin linker 1 | 2.04 | 4.E-05 | 2.71 | 1.3E-05 |
| PELO; ITGA1 | pelota homolog (Dros); integrin alpha 1 | -2.53 | 2.E-04 | -2.07 | 3.7E-03 |
| SLCO4C1 | SLC transporter family, member 4C1 | -4.70 | 6.E-07 | -3.26 | 3.8E-05 |
| ID4 | inhibitor of DNA binding 4, dominant - HLHP | -2.60 | 7.E-05 | -2.34 | 3.0E-04 |
| SOX4 | SRY box 4 | -3.30 | 6.E-07 | -2.44 | 6.2E-05 |
| HIST1H2BM | histone cluster 1, H2bm | -2.76 | 1.E-02 | -3.51 | 5.6E-03 |
| CFB | complement factor B | -2.16 | 1.E-03 | -2.00 | 8.6E-03 |
| CENPW | centromere protein W | 2.05 | 3.E-03 | 2.17 | 2.7E-03 |
| LPAL2 | lipoprotein, Lp(a)-like 2, pseudogene | -2.71 | 9.E-05 | -2.07 | 1.0E-03 |
| CLDN12 | claudin 12 | 2.21 | 2.E-05 | 2.59 | 1.6E-05 |
| LOC340340 | uncharacterized LOC340340 | -3.25 | 1.E-06 | -2.15 | 4.0E-04 |
| RASA4B | RAS p21 protein activator 4B; RAS p21 protein activator 4 | -2.14 | 2.E-02 | -2.51 | 1.0E-02 |
| CLIC3 | chloride intracellular channel 3 | -2.07 | 9.E-05 | -2.01 | 7.0E-04 |
| SAT1 | spermidine/spermine N1-AC 1 | -2.41 | 7.E-05 | -2.02 | 1.3E-03 |
| CA12 | carbonic anhydrase XII | -4.41 | 2.E-07 | -3.07 | 2.5E-05 |
| CA13 | centrosomal protein 152kDa | 2.12 | 6.E-03 | 2.00 | 2.1E-02 |

FIG. 7 cont.

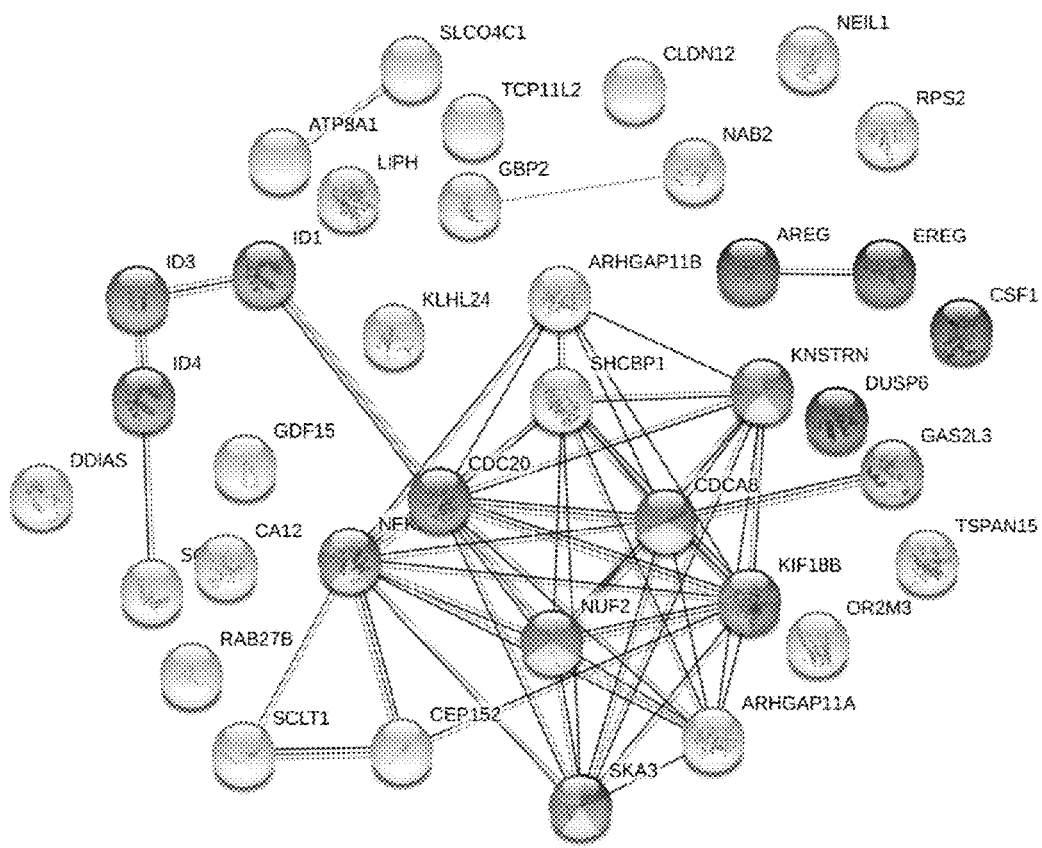

Overlapping DEGs by GM-4-53 and Taxol

| ID | Go-Term | Description | Count in Network | Strength | FDR | Color Code |
|---|---|---|---|---|---|---|
| Biological Process | | | | | | |
| Go Term | GO:0000070 | Mitotic Sister Chromatid Segregation | 5 of 110 | 1.42 | 1.1 x 10-3 | |
| Go Term | GO:0051988 | Spindle Microtubules to Kinectochore | 2 of 12 | 1.95 | 1.8 x 10-2 | |
| Cellular Component (Gene Ontology) | | | | | | |
| Go Term | GO:0005876 | Spindle Microtubules | 2 of 47 | 1.35 | 4.1 x 10-2 | |
| Go Term | GO:000777 | Condensed Chromosome Kinetochore | 4 of 104 | 1.31 | 2.3 x 10-3 | |
| Go Term | GO:0000775 | Chromosome : Centrometric Region | 5 of 189 | 1.15 | 1.9 x 10-3 | |
| KEGG Pathways | | | | | | |
| Pathway | hsa04350 | TGF-beta Signaling Pathway | 3 of 83 | 1.28 | 1.6 x 10-2 | |
| Pathway | hsa04010 | MAPK Signaling Pathway | 4 of 293 | 0.86 | 3.2 x 10-2 | |
| Annotated Keywords (UniProt) | | | | | | |
| Keyword | KW-0498 | Mitosis | 7 of 268 | 1.14 | 7.8 x 10-5 | |
| Keyword | KW-0493 | Microtubule | 5 of 275 | 0.98 | 2.1 x 10-3 | |

FDR = False Discovery Rate, Color Code = String Mode Ball Gene Symbol Match

FIG. 8

|  |  | Paclitaxel | | | GM-4-83 | | |
|---|---|---|---|---|---|---|---|
| Symbol | Description | FC | p-Value | FDR p-Value | FC | p-Value | FDR p-Value |
| AREG | amphiregulin | −3.06 | 1.0 × 10⁻⁴ | 2.5 × 10⁻² | −2.74 | 1.0 × 10⁻⁶ | 1.2 × 10⁻⁴ |
| ARHGAP11A | Rho GTPase activating protein 11A | 2.64 | 3.3 × 10⁻⁶ | 1.2 × 10⁻³ | 2.08 | 3.3 × 10⁻⁶ | 1.1 × 10⁻³ |
| ARHGAP11B | Rho GTPase activating protein 11B | 3.10 | 6.8 × 10⁻⁶ | 5.3 × 10⁻³ | 2.38 | 3.9 × 10⁻⁵ | 5.5 × 10⁻³ |
| ATP8A1 | ATPase, (APLT), class I, 8A, m1 | −2.27 | 2.2 × 10⁻⁶ | 3.3 × 10⁻³ | −2.88 | 4.9 × 10⁻⁹ | 1.7 × 10⁻⁵ |
| CA12 | carbonic anhydrase XII | −3.17 | 8.6 × 10⁻⁸ | 5.0 × 10⁻⁴ | −4.88 | 3.0 × 10⁻¹¹ | 1.3 × 10⁻⁶ |
| CDC20 | cell division cycle 20 | 2.49 | 3.0 × 10⁻⁴ | 4.2 × 10⁻² | 2.11 | 7.0 × 10⁻⁴ | 3.5 × 10⁻² |
| CDCA8 | cell division cycle associated 8 | 2.30 | 6.7 × 10⁻⁵ | 1.9 × 10⁻² | 2.20 | 3.2 × 10⁻⁵ | 4.9 × 10⁻³ |
| CEP152 | centrosomal protein 152 kDa | 2.25 | 2.0 × 10⁻⁴ | 3.4 × 10⁻² | 2.41 | 3.6 × 10⁻⁵ | 5.2 × 10⁻³ |
| CLDN12 | claudin 12 | 3.07 | 1.6 × 10⁻⁷ | 8.0 × 10⁻⁴ | 2.11 | 5.0 × 10⁻⁶ | 1.4 × 10⁻³ |
| CSF1 | colony stimulating factor 1 | −2.27 | 2.1 × 10⁻⁶ | 3.3 × 10⁻³ | −3.70 | 8.8 × 10⁻¹¹ | 1.3 × 10⁻⁶ |
| DDIAS | DNA damage-induced apoptosis suppressor | 2.13 | 1.6 × 10⁻⁵ | 2.8 × 10⁻³ | 2.11 | 7.1 × 10⁻⁷ | 4.0 × 10⁻⁴ |
| DUSP6 | dual specificity phosphatase 6 | −2.21 | 9.2 × 10⁻⁸ | 5.0 × 10⁻⁴ | −2.86 | 8.8 × 10⁻¹¹ | 1.3 × 10⁻⁶ |
| EREG | epiregulin | −3.19 | 8.6 × 10⁻⁵ | 2.1 × 10⁻² | −2.96 | 9.4 × 10⁻⁶ | 2.2 × 10⁻³ |
| GAS2L3 | growth arrest-specific 2 like 3 | 2.81 | 7.9 × 10⁻⁶ | 5.8 × 10⁻³ | 2.08 | 5.9 × 10⁻⁵ | 7.3 × 10⁻³ |
| GBP2 | guanylate binding protein 2, interferon-inducible | −2.81 | 1.7 × 10⁻⁵ | 8.6 × 10⁻³ | −3.00 | 1.2 × 10⁻⁶ | 6.0 × 10⁻⁴ |
| GDF15 | growth differentiation factor 15 | −2.18 | 4.0 × 10⁻⁴ | 4.2 × 10⁻² | −2.03 | 6.0 × 10⁻⁵ | 7.3 × 10⁻³ |
| ID1 | inhibitor of DNA binding 1, dom-HLHP | −2.15 | 2.0 × 10⁻⁴ | 3.2 × 10⁻² | −5.43 | 1.3 × 10⁻¹⁰ | 1.3 × 10⁻⁶ |
| ID3 | inhibitor of DNA binding 3, dom-HLHP | −2.21 | 8.5 × 10⁻⁴ | 2.1 × 10⁻² | −4.32 | 1.4 × 10⁻¹⁰ | 1.3 × 10⁻⁶ |
| ID4 | inhibitor of DNA binding 4, dom-HLHP | −2.49 | 1.0 × 10⁻⁵ | 6.2 × 10⁻³ | −3.36 | 1.4 × 10⁻⁷ | 1.0 × 10⁻⁴ |
| KIF18B | kinesin family member 18B | 2.19 | 2.8 × 10⁻⁵ | 1.2 × 10⁻² | 2.24 | 5.2 × 10⁻⁶ | 1.4 × 10⁻³ |
| KLHL24 | kelch-like family member 24 | −2.12 | 1.0 × 10⁻⁴ | 2.7 × 10⁻² | −2.62 | 7.6 × 10⁻⁷ | 4.0 × 10⁻⁴ |
| KNSTRN | kinetochore-loc. astrin/SPAG5bp | 2.80 | 3.6 × 10⁻⁷ | 1.2 × 10⁻³ | 2.15 | 4.5 × 10⁻⁶ | 1.3 × 10⁻³ |
| LIPH | lipase, member H | −2.51 | 2.5 × 10⁻⁶ | 3.4 × 10⁻³ | −2.38 | 8.8 × 10⁻⁷ | 5.0 × 10⁻⁴ |
| LPAL2 | lipoprotein, Lp(a)-like 2, pg | −2.11 | 4.0 × 10⁻⁴ | 4.6 × 10⁻² | −2.58 | 1.3 × 10⁻⁵ | 2.6 × 10⁻³ |
| NAB2 | NGFI-A binding protein 2 (EGR1 binding protein 2) | −2.05 | 3.0 × 10⁻⁴ | 3.9 × 10⁻² | −2.29 | 8.6 × 10⁻⁶ | 2.0 × 10⁻³ |
| NEIL1 | nei-like DNA glycosylase 1 | −2.01 | 4.7 × 10⁻⁵ | 1.5 × 10⁻² | −2.31 | 6.5 × 10⁻⁷ | 4.0 × 10⁻⁴ |
| NEK2 | NIMA-related kinase 2 | 3.06 | 4.7 × 10⁻⁵ | 1.5 × 10⁻² | 2.00 | 7.0 × 10⁻⁴ | 3.5 × 10⁻² |
| NUF2 | NUF2, NDC80 kinetochore com c | 2.67 | 3.9 × 10⁻⁵ | 1.7 × 10⁻² | 2.03 | 5.0 × 10⁻⁵ | 2.9 × 10⁻³ |
| PELO; ITGA1 | pelota hom (Dros); integrin alpha 1 | −2.21 | 2.0 × 10⁻⁴ | 3.5 × 10⁻² | −2.66 | 2.3 × 10⁻⁶ | 8.0 × 10⁻⁴ |
| RAB27B | RAB27B, member RAS oncogene family | −2.26 | 4.1 × 10⁻⁵ | 1.5 × 10⁻² | −2.27 | 1.1 × 10⁻⁶ | 6.0 × 10⁻⁴ |
| RPS2 | ribosomal protein S2 | 3.17 | 5.4 × 10⁻⁵ | 1.7 × 10⁻³ | 2.41 | 3.3 × 10⁻⁶ | 1.1 × 10⁻³ |
| SCLT1 | sodium channel/clathrin linker 1 | 3.09 | 2.7 × 10⁻⁵ | 1.1 × 10⁻² | 2.30 | 3.5 × 10⁻⁶ | 1.1 × 10⁻³ |
| SHCBP1 | SHC SH2-domain binding protein 1 | 2.39 | 5.1 × 10⁻⁵ | 1.6 × 10⁻² | 2.06 | 6.4 × 10⁻⁵ | 7.7 × 10⁻³ |
| SKA3 | Spindle & Kinetochore complex s3 | 2.33 | 1.0 × 10⁻⁴ | 2.7 × 10⁻² | 2.12 | 2.0 × 10⁻⁴ | 1.3 × 10⁻² |
| SLCO4C1 | SC organic anion transporter fm4C1 | −3.40 | 3.7 × 10⁻⁶ | 4.0 × 10⁻³ | −4.53 | 1.2 × 10⁻⁸ | 2.8 × 10⁻⁵ |
| SOX4 | SRY box 4 | −2.31 | 5.4 × 10⁻⁶ | 4.9 × 10⁻³ | −3.08 | 2.0 × 10⁻⁸ | 9.6 × 10⁻⁵ |
| TSPAN15 | tetraspanin 15 | −2.31 | 1.1 × 10⁻⁵ | 2.3 × 10⁻³ | −2.41 | 9.7 × 10⁻⁵ | 1.0 × 10⁻⁴ |

FIG. 10

| Gene Symbol | Description | Control Avg (log2) | GM4-53 Avg (log2) | Fold Change | P-Val | FDR P-Val |
|---|---|---|---|---|---|---|
| FOS | FBJ murine osteosarcoma viral oncogene homolog | 5.61 | 3.30 | -5.0 | 6.30E-03 | 1.34E-01 |
| GBP4 | guanylate binding protein 4 | 3.96 | 2.00 | -4.8 | 3.73E-07 | 9.00E-04 |
| ZNF608 | zinc finger protein 608 | 5.38 | 3.45 | -3.8 | 6.78E-07 | 9.00E-04 |
| KLRC4-KLRK1 | KLRC4-KLRK1 readthrough; KCLL K, 1 C,4 | 3.74 | 1.90 | -3.6 | 1.30E-03 | 5.83E-02 |
| MAP3K8 | mitogen-activated protein kinase kinase kinase 8 | 3.44 | 1.76 | -3.2 | 4.56E-02 | 3.42E-01 |
| TNFSF18 | tumor necrosis factor (ligand) superfamily, member 18 | 3.79 | 2.14 | -3.1 | 5.30E-03 | 1.23E-01 |
| RARRES3 | retinoic acid receptor responder (tazarotene induced) 3 | 5.16 | 3.80 | -3.0 | 5.46E-07 | 9.00E-04 |
| TRIB2 | tribbles pseudokinase 2 | 6.97 | 4.43 | -2.9 | 2.58E-07 | 8.00E-04 |
| TLR3 | toll-like receptor 3 | 4.52 | 2.99 | -2.9 | 2.00E-04 | 2.32E-02 |
| HES1 | hes family bHLH transcription factor 1 | 5.56 | 4.04 | -2.9 | 4.26E-07 | 9.00E-04 |
| SCNN1A | sodium channel, non-voltage gated 1 alpha subunit | 6.13 | 4.62 | -2.9 | 6.84E-08 | 6.00E-04 |
| TNFSF10 | tumor necrosis factor (ligand) superfamily, member 10 | 6.46 | 4.95 | -2.8 | 1.00E-04 | 1.61E-02 |
| GBP2 | guanylate binding protein 2, interferon-inducible | 5.13 | 3.64 | -2.8 | 8.00E-04 | 3.71E-02 |
| HLA-DRA | major histocompatibility complex, class II, DR alpha | 8.02 | 6.53 | -2.8 | 7.52E-05 | 1.17E-02 |
| SMAD6 | SMAD family member 6 | 3.72 | 2.24 | -2.8 | 5.00E-04 | 3.27E-02 |
| LOC | uncharacterized LOC100507521 | 2.95 | 1.47 | -2.8 | 2.12E-02 | 2.41E-01 |
| LOC | uncharacterized LOC105377283 | 2.88 | 1.42 | -2.8 | 8.40E-03 | 1.54E-01 |
| FAM43A | family with sequence similarity 43, member A | 4.86 | 3.41 | -2.7 | 1.27E-06 | 1.30E-03 |
| SESN3 | sestrin 3 | 4.43 | 3.00 | -2.7 | 7.36E-06 | 3.40E-03 |
| METTL7A | methyltransferase like 7A | 5.16 | 3.74 | -2.7 | 9.22E-06 | 3.90E-03 |
| MARCKSL1 | MARCKS-like 1 | 4.80 | 3.41 | -2.6 | 3.37E-06 | 2.20E-03 |
| TNFRSF9 | tumor necrosis factor receptor superfamily, member 9 | 3.60 | 2.24 | -2.6 | 2.32E-05 | 6.40E-03 |
| LOC | uncharacterized LOC105376517 | 4.47 | 3.10 | -2.6 | 6.05E-05 | 1.04E-02 |
| CDH11 | cadherin 11, type 2, OB-cadherin (osteoblast) | 7.68 | 6.34 | -2.6 | 2.00E-04 | 2.03E-02 |
| FBXL20 | f-box and leucine-rich repeat protein 20 | 5.75 | 4.40 | -2.5 | 2.63E-07 | 8.00E-04 |
| CTSO | cathepsin O | 5.42 | 4.08 | -2.5 | 3.95E-05 | 8.20E-03 |
| ADAM28 | ADAM metallopeptidase domain 28 | 4.02 | 2.68 | -2.5 | 2.53E-05 | 6.80E-03 |
| LOC | uncharacterized LOC100506885 | 4.24 | 2.91 | -2.5 | 4.00E-04 | 2.90E-02 |
| ETV1 | ets variant 1 | 6.81 | 5.47 | -2.5 | 2.41E-07 | 8.00E-04 |
| SLC43A2 | solute carrier family 43, member 2 | 4.60 | 3.28 | -2.5 | 5.00E-04 | 3.50E-02 |
| SLC20A1 | solute carrier family 20, member 1 | 9.06 | 7.76 | -2.5 | 3.94E-07 | 9.00E-04 |
| MAP3K5 | mitogen-activated protein kinase kinase kinase 5 | 5.90 | 4.59 | -2.5 | 3.00E-04 | 2.55E-02 |
| SLC38A4 | solute carrier family 38, member 4 | 4.20 | 2.90 | -2.5 | 4.50E-03 | 1.12E-01 |

FIG. 12

| Gene | Description | | | | | |
|---|---|---|---|---|---|---|
| CADPS2 | Ca++-dependent secretion activator 2 | 5.38 | 4.08 | -2.5 | 1.00E-04 | 1.58E-02 |
| IFIT1 | interferon-induced protein with tetratricopeptide repeats 1 | 3.79 | 2.49 | -2.5 | 1.00E-04 | 1.72E-02 |
| IGHV1-58 | immunoglobulin heavy variable 1-58 | 3.80 | 2.51 | -2.5 | 3.90E-03 | 1.03E-01 |
| SPDEF | SAM pointed domain containing ETS transcription factor | 5.78 | 4.47 | -2.5 | 3.71E-06 | 2.20E-03 |
| PRICKLE2 | prickle homolog 2 | 5.02 | 3.73 | -2.5 | 3.61E-05 | 7.90E-03 |
| PCDHB8 | protocadherin beta 8 | 4.06 | 2.77 | -2.4 | 1.50E-03 | 6.04E-02 |
| HLA-DPB1 | major histocompatibility complex, class II, DP beta 1 | 5.46 | 4.17 | -2.4 | 3.57E-06 | 2.20E-03 |
| SLC44A5 | solute carrier family 44, member 5 | 5.69 | 4.41 | -2.4 | 1.66E-06 | 1.40E-03 |
| MUC1 | mucin 1, cell surface associated | 5.57 | 4.29 | -2.4 | 4.00E-04 | 3.17E-02 |
| OASL | 2-5-oligoadenylate synthetase-like | 4.47 | 3.19 | -2.4 | 1.03E-07 | 6.00E-04 |
| CMKLR1 | chemerin chemokine-like receptor 1 | 5.33 | 4.06 | -2.4 | 5.76E-07 | 9.00E-04 |
| MYO1F | myosin IF | 4.56 | 3.28 | -2.4 | 4.08E-06 | 2.40E-03 |
| H1F0 | H1 histone family, member 0 | 7.53 | 6.27 | -2.4 | 4.59E-08 | 4.00E-04 |
| APOL6 | apolipoprotein L, 6 | 5.49 | 4.24 | -2.4 | 4.48E-05 | 8.70E-03 |
| SAA2-SAA4 | serum amyloid SAA2-SAA4 readthrough;constitutive | 3.53 | 2.29 | -2.4 | 5.90E-03 | 1.30E-01 |
| PCDHB12 | protocadherin beta 12 | 4.85 | 3.60 | -2.4 | 3.30E-03 | 9.35E-02 |
| ZNF117 | zinc finger protein 117 | 4.01 | 2.77 | -2.4 | 1.70E-03 | 6.56E-02 |
| CFH | complement factor H | 5.17 | 3.94 | -2.4 | 3.00E-04 | 2.60E-02 |
| ZNF436 | zinc finger protein 436 | 5.04 | 3.81 | -2.4 | 1.00E-03 | 4.77E-02 |
| PNRC1 | proline-rich nuclear receptor coactivator 1 | 6.57 | 5.34 | -2.4 | 2.80E-05 | 7.10E-03 |
| SAMD9L | sterile alpha motif domain containing 9-like | 5.06 | 3.82 | -2.4 | 4.37E-05 | 8.70E-03 |
| IFI44 | interferon-induced protein 44 | 5.27 | 4.04 | -2.3 | 2.71E-05 | 6.90E-03 |
| ZNF525 | zinc finger protein 525 | 4.16 | 2.95 | -2.3 | 2.70E-03 | 8.61E-02 |
| FAM89B | family with sequence similarity 89,B | 6.47 | 5.26 | -2.3 | 8.41E-07 | 1.00E-03 |
| SPRY1 | sprouty RTK signaling antagonist 1 | 6.15 | 4.96 | -2.3 | 3.45E-07 | 9.00E-04 |
| NAB2 | NGFI-A binding protein 2 (EGR1 binding protein 2) | 4.84 | 3.45 | -2.3 | 3.00E-04 | 2.87E-02 |
| NEIL1 | nei-like DNA glycosylase 1 | 4.34 | 3.16 | -2.3 | 1.02E-05 | 4.20E-03 |
| TNS4 | tensin 4 | 6.29 | 5.11 | -2.3 | 5.12E-07 | 9.00E-04 |
| NUPR1 | nuclear protein 1, transcriptional regulator | 5.81 | 4.65 | -2.2 | 3.30E-02 | 2.96E-01 |
| REEP6 | receptor accessory protein 6 | 5.13 | 3.97 | -2.2 | 3.33E-07 | 9.00E-04 |
| ST6GAL1 | ST6 beta-galactosamide alpha-2,6-sialyltranferase 1 | 3.43 | 2.27 | -2.2 | 2.70E-03 | 8.51E-02 |
| THBS3 | thrombospondin 3 | 4.15 | 2.89 | -2.2 | 5.97E-05 | 1.04E-02 |
| SGK223 | homolog of rat pragma of Rnd2 | 5.79 | 4.65 | -2.2 | 1.80E-07 | 8.00E-04 |
| PDIA3P1 | protein disulfide isomerase family A member 3 | 4.62 | 3.49 | -2.2 | 1.90E-03 | 7.03E-02 |
| LOC | uncharacterized LOC105376382 | 3.58 | 2.44 | -2.2 | 2.04E-05 | 6.10E-03 |
| OAS1 | 2-5-oligoadenylate synthetase 1 | 3.36 | 2.24 | -2.2 | 6.30E-07 | 9.00E-04 |
| ABHD4 | abhydrolase domain containing 4 | 5.07 | 3.95 | -2.2 | 4.45E-05 | 8.70E-03 |
| RGL1 | ral guanine nucleotide dissociation stimulator-like 1 | 4.80 | 3.69 | -2.2 | 5.67E-05 | 1.01E-02 |
| PARD6B | par-6 family cell polarity regulator beta | 6.76 | 5.65 | -2.2 | 2.91E-05 | 7.10E-03 |
| OAS2 | 2-5-oligoadenylate synthetase 2 | 4.80 | 3.70 | -2.2 | 2.00E-04 | 1.80E-02 |

FIG. 12 cont.

| Gene | Description | | | | |
|---|---|---|---|---|---|
| TIMP3 | TIMP metallopeptidase inhibitor 3 | 9.49 | 8.38 | -2.2 | 1.14E-05 4.50E-03 |
| MUC15 | mucin 15, cell surface associated | 3.68 | 2.58 | -2.1 | 7.60E-03 1.47E-01 |
| IER5L | immediate early response 5-like | 4.33 | 3.24 | -2.1 | 3.42E-05 7.70E-03 |
| EFNA1 | ephrin-A1 | 4.18 | 3.09 | -2.1 | 2.40E-03 7.94E-02 |
| MIR4324 | microRNA 4324 | 4.06 | 2.99 | -2.1 | 4.70E-03 1.14E-01 |
| CYP1B1 | cytochrome P450, family 1, subfamily B, polypeptide 1 | 6.36 | 5.26 | -2.1 | 2.60E-03 8.67E-02 |
| NR4A2 | nuclear receptor subfamily 4, group A, member 2 | 4.96 | 3.85 | -2.1 | 4.15E-06 2.40E-03 |
| ARL6IP5 | ADP-ribosylation factor like GTPase 6 IP 5 | 8.82 | 7.72 | -2.1 | 8.38E-06 3.80E-03 |
| MZF1 | myeloid zinc finger 1 | 4.10 | 3.02 | -2.1 | 4.50E-03 1.11E-01 |
| SMIM14 | small integral membrane protein 14 | 5.72 | 4.63 | -2.1 | 2.00E-04 2.16E-02 |
| PLXDC2 | plexin domain containing 2 | 6.10 | 5.02 | -2.1 | 8.78E-06 3.90E-03 |
| VWA5A | von Willebrand factor A domain containing 5A | 3.56 | 2.49 | -2.1 | 9.00E-04 4.69E-02 |
| SLC37A2 | solute carrier family 37 (glucose-6-phosphate transporter) 2 | 7.59 | 6.51 | -2.1 | 9.13E-06 3.90E-03 |
| CDON | cell adhesion associated, oncogene regulated | 5.67 | 4.59 | -2.1 | 1.32E-05 4.90E-03 |
| MSMO1 | methylsterol monooxygenase 1 | 7.97 | 6.89 | -2.1 | 3.60E-03 9.96E-02 |
| TRBV30 | T cell receptor beta variable 30 (gene/pseudogene) | 2.94 | 1.86 | -2.1 | 1.59E-02 2.12E-01 |
| GRHL2 | grainyhead-like transcription factor 2 | 5.12 | 4.05 | -2.1 | 1.31E-05 4.90E-03 |
| CNTNAP3 | contactin associated protein-like 3 | 5.41 | 4.34 | -2.1 | 2.00E-04 2.18E-02 |
| KLHL4 | kelch-like family member 4 | 6.07 | 5.00 | -2.1 | 2.20E-03 7.84E-02 |
| JUNB | jun B proto-oncogene | 5.69 | 4.62 | -2.1 | 3.33E-06 2.20E-03 |
| ALG1L2 | ALG1, chitobiosyldiphosphodolichol beta-mannosyltransferase-like 2 | 3.18 | 2.11 | -2.1 | 1.85E-02 2.28E-01 |
| KLHL24 | kelch-like family member 24 | 5.21 | 4.14 | -2.1 | 6.00E-04 3.82E-02 |
| CD14 | CD14 molecule | 3.22 | 2.15 | -2.1 | 1.30E-03 5.65E-02 |
| MIR23B | microRNA 23b; chromosome 9 open reading frame 3 | 4.74 | 3.68 | -2.1 | 2.90E-03 8.84E-02 |
| GABARAPL1 | GABA(A) receptor-associated protein like 1 | 4.57 | 3.51 | -2.1 | 1.06E-05 4.40E-03 |
| ZG16B | zymogen granule protein 16B | 5.22 | 4.17 | -2.1 | 3.00E-04 2.50E-02 |
| IDH1 | isocitrate dehydrogenase 1 (NADP+) | 5.30 | 4.25 | -2.1 | 9.66E-07 1.10E-03 |
| FANCF | Fanconi anemia complementation group F | 4.28 | 3.24 | -2.1 | 5.00E-04 3.60E-02 |
| LILRB1 | leukocyte immunoglobulin-like receptor, B, member 1 | 6.18 | 5.13 | -2.1 | 4.32E-05 8.80E-03 |
| SLCO4A1 | solute carrier organic anion transporter family,4A1 | 5.23 | 4.18 | -2.1 | 1.30E-03 5.74E-02 |
| DDIT4 | DNA damage inducible transcript 4 | 6.89 | 5.85 | -2.1 | 4.76E-06 2.60E-03 |
| IFIT3 | interferon-induced protein with tetratricopeptide repeats 3 | 5.32 | 4.28 | -2.1 | 7.00E-04 3.96E-02 |
| UBE2L6 | ubiquitin-conjugating enzyme E2L 6 | 3.90 | 2.86 | -2.1 | 4.45E-05 8.70E-03 |
| HCAR1 | hydroxycarboxylic acid receptor 1 | 3.91 | 2.87 | -2.1 | 4.44E-06 2.50E-03 |
| PLSCR4 | phospholipid scramblase 4 | 3.96 | 2.91 | -2.1 | 1.11E-05 4.50E-03 |
| PCDHB10 | protocadherin beta 10 | 5.01 | 3.96 | -2.1 | 2.86E-05 6.90E-03 |
| SORL1 | sortilin-related receptor, L(DLR class) A repeats containing | 5.05 | 4.01 | -2.1 | 1.86E-06 1.40E-03 |
| LGR5 | leucine-rich repeat containing G protein-coupled receptor 5 | 4.00 | 2.97 | -2.1 | 4.18E-05 8.50E-03 |
| KCTD12 | potassium channel tetramerization domain | 6.15 | 5.12 | -2.0 | 5.84E-05 1.02E-02 |

FIG. 12 cont.

| Gene | Description | Val1 | Val2 | FC | p-val1 | p-val2 |
|---|---|---|---|---|---|---|
| | containing 12 | | | | | |
| PPL | periplakin | 5.00 | 3.97 | -2.0 | 3.62E-06 | 2.20E-03 |
| FZD3 | frizzled class receptor 3 | 3.06 | 2.03 | -2.0 | 8.80E-03 | 1.57E-01 |
| TSPAN8 | tetraspanin 8 | 4.49 | 3.46 | -2.0 | 2.50E-03 | 8.30E-02 |
| YPEL3 | yippee like 3 | 4.06 | 3.03 | -2.0 | 1.20E-03 | 5.38E-02 |
| CLDN7 | claudin 7 | 6.07 | 5.04 | -2.0 | 4.03E-05 | 8.30E-03 |
| RIPK4 | receptor-interacting serine-threonine kinase 4 | 4.04 | 3.02 | -2.0 | 3.00E-03 | 8.91E-02 |
| GALR3 | galanin receptor 3 | 3.82 | 2.80 | -2.0 | 3.78E-02 | 3.15E-01 |
| TRANK1 | tetratricopeptide repeat and ankyrin repeat containing 1 | 3.69 | 2.67 | -2.0 | 1.00E-04 | 1.72E-02 |
| LOXL4 | lysyl oxidase-like 4 | 4.26 | 3.24 | -2.0 | 1.14E-06 | 1.20E-03 |
| LRP5 | LDL receptor related protein 5 | 6.68 | 5.67 | -2.0 | 2.11E-05 | 6.20E-03 |
| NNMT | nicotinamide N-methyltransferase | 4.38 | 3.37 | -2.0 | 2.90E-03 | 8.77E-02 |
| LOC105369316 | uncharacterized LOC105369316 | 3.55 | 2.54 | -2.0 | 4.90E-03 | 1.18E-01 |
| ACSS3 | acyl-CoA synthetase short-chain family member 3 | 6.16 | 5.15 | -2.0 | 7.04E-06 | 3.40E-03 |
| HLA-DMA/B | major histocompatibility complex, class II, DM alpha; major histocompatibility complex, class II, DM beta | 5.48 | 4.47 | -2.0 | 1.62E-05 | 5.70E-03 |
| HLA-DPA1 | major histocompatibility complex, class II, DP alpha 1 | 4.94 | 3.93 | -2.0 | 7.00E-04 | 4.21E-02 |
| FLJ22447 | uncharacterized LOC400221 | 4.90 | 3.89 | -2.0 | 8.28E-05 | 1.25E-02 |
| NFKBIA | nuclear factor of kappa light polypeptide gene enhancer in B-cells inhibitor, alpha | 6.51 | 5.50 | -2.0 | 2.44E-05 | 6.60E-03 |
| ARRDC3 | arrestin domain containing 3 | 7.10 | 6.10 | -2.0 | 3.34E-06 | 2.20E-03 |
| ITFG1 | integrin alpha FG-GAP repeat containing 1 | 2.93 | 1.92 | -2.0 | 8.80E-03 | 1.37E-01 |
| MIR1278 | microRNA 1278 | 1.06 | 2.06 | 2.0 | 2.50E-03 | 8.30E-02 |
| MIR656 | microRNA 656 | 1.48 | 2.48 | 2.0 | 3.00E-04 | 2.82E-02 |
| HIF1A-AS2 | HIF1A antisense RNA 2 | 4.99 | 6.01 | 2.0 | 7.06E-06 | 3.40E-03 |
| KIF18B | kinesin family member 18B | 5.95 | 6.96 | 2.0 | 3.00E-04 | 2.72E-02 |
| MB21D2 | Mab-21 domain containing 2 | 3.64 | 4.66 | 2.0 | 7.26E-05 | 1.14E-02 |
| IQGAP3 | IQ motif containing GTPase activating protein 3 | 6.03 | 7.06 | 2.0 | 8.00E-04 | 4.31E-02 |
| BEND7 | BEN domain containing 7 | 4.13 | 5.16 | 2.0 | 4.23E-05 | 8.50E-03 |
| ADGRG6 | adhesion G protein-coupled receptor G6 | 5.76 | 6.80 | 2.1 | 7.31E-06 | 3.40E-03 |
| CXCR4 | chemokine (C-X-C motif) receptor 4 | 3.86 | 4.90 | 2.1 | 4.00E-04 | 2.91E-02 |
| EHMT1-IT1 | EHMT1 intronic transcript 1 | 4.24 | 5.29 | 2.1 | 8.00E-04 | 4.51E-02 |
| ZNF799 | zinc finger protein 799 | 1.76 | 2.81 | 2.1 | 3.76E-02 | 3.14E-01 |
| MICALL1 | MICAL-like 1 | 3.71 | 4.77 | 2.1 | 1.00E-04 | 1.46E-02 |
| DRP2 | dystrophin related protein 2 | 3.02 | 4.07 | 2.1 | 1.30E-03 | 5.74E-02 |
| ZNF185 | zinc finger protein 185 (LIM domain) | 5.83 | 6.89 | 2.1 | 8.00E-04 | 4.25E-02 |
| NEDD4L | neural precursor cell expressed, developmentally down-regulated 4-like, E3 ubiquitin protein ligase | 7.37 | 8.43 | 2.1 | 4.48E-07 | 9.00E-04 |
| SERPINE1 | serpin peptidase inhibitor, clade E (nexin, plasminogen activator inhibitor type 1), member 1 | 7.56 | 8.62 | 2.1 | 7.06E-07 | 9.00E-04 |
| NEXN | nexilin (F actin binding protein) | 4.70 | 5.77 | 2.1 | 1.73E-05 | 5.70E-03 |
| OPHN1 | oligophrenin 1 | 6.10 | 8.18 | 2.1 | 3.00E-04 | 2.78E-02 |
| LOC728093; 643784; | putative POM121-like protein 1-like; NLR family, apoptosis inhibitory protein pseudogene | 1.64 | 2.73 | 2.1 | 3.47E-06 | 7.70E-03 |

FIG. 12 cont.

| | | | | | | |
|---|---|---|---|---|---|---|
| 102725182 | | | | | | |
| COL8A1 | collagen, type VIII, alpha 1 | 4.20 | 5.30 | 2.1 | 4.00E-04 | 2.85E-02 |
| OR4D10 | olfactory receptor, family 4, subfamily D, member 10 | 1.96 | 3.06 | 2.2 | 4.10E-03 | 1.06E-01 |
| KCNQ5 | potassium channel, voltage gated KQT-like subfamily Q, member 5 | 4.38 | 5.48 | 2.2 | 2.30E-03 | 7.81E-02 |
| FANCB | Fanconi anemia complementation group B | 3.39 | 4.50 | 2.2 | 1.30E-02 | 1.93E-01 |
| TAGLN | transgelin | 2.68 | 3.79 | 2.2 | 1.32E-05 | 4.90E-03 |
| FLNC | filamin C, gamma | 6.14 | 7.26 | 2.2 | 2.11E-05 | 6.20E-03 |
| NRK | Nik related kinase | 1.98 | 3.10 | 2.2 | 3.55E-06 | 2.20E-03 |
| ZNF92 | zinc finger protein 92 | 2.64 | 3.79 | 2.2 | 4.96E-02 | 3.44E-01 |
| PGM2 | phosphoglucomutase 2 | 6.22 | 7.38 | 2.2 | 9.00E-04 | 4.61E-02 |
| LPP | LIM domain containing preferred translocation partner in lipoma | 3.72 | 4.89 | 2.2 | 6.00E-04 | 3.81E-02 |
| SAMD4A | sterile alpha motif domain containing 4A | 4.17 | 5.34 | 2.3 | 2.25E-06 | 1.80E-03 |
| POM121 | POM121 transmembrane nucleoporin | 4.42 | 5.60 | 2.3 | 4.00E-04 | 3.07E-02 |
| NEGR1 | neuronal growth regulator 1 | 4.28 | 5.47 | 2.3 | 1.00E-04 | 1.46E-02 |
| STARD13 | StAR-related lipid transfer domain containing 13 | 2.88 | 4.07 | 2.3 | 1.00E-06 | 1.10E-03 |
| SNORA75 | small nucleolar RNA, H/ACA box 75 | 6.78 | 7.97 | 2.3 | 1.80E-06 | 1.50E-03 |
| CDC14B | cell division cycle 14B | 1.80 | 2.99 | 2.3 | 2.24E-02 | 2.48E-01 |
| SNRPN; IPW | small nuclear ribonucleoprotein polypeptide N; imprinted in Prader-Willi syndrome (non-protein coding) | 2.75 | 3.95 | 2.3 | 1.00E-04 | 1.58E-02 |
| SEMA7A | semaphorin 7A, GPI membrane anchor (John Milton Hagen blood group) | 4.92 | 6.13 | 2.3 | 1.00E-04 | 1.54E-02 |
| ARHGEF26 | Rho guanine nucleotide exchange factor 26 | 3.95 | 5.16 | 2.3 | 5.00E-04 | 3.80E-02 |
| RPL23AP49 | ribosomal protein L23a pseudogene 49 | 2.35 | 3.57 | 2.3 | 3.00E-04 | 2.46E-02 |
| SNORD11B | small nucleolar RNA, C/D box 11B | 3.47 | 4.69 | 2.3 | 1.20E-03 | 5.50E-02 |
| NFATC2 | nuclear factor of activated T-cells, cytoplasmic, calcineurin-dependent 2 | 4.82 | 6.05 | 2.3 | 5.32E-05 | 9.70E-03 |
| NF2 | neurofibromin 2 (merlin) | 4.22 | 5.46 | 2.4 | 4.24E-07 | 9.00E-04 |
| MIR3116-1 | microRNA 3116-1 | 3.12 | 4.36 | 2.4 | 7.80E-03 | 1.48E-01 |
| LOC100133106 | VCEW9374 | 3.63 | 4.87 | 2.4 | 1.47E-02 | 2.03E-01 |
| SAMD12-AS1 | SAMD12 antisense RNA 1 | 2.11 | 3.35 | 2.4 | 1.50E-03 | 6.06E-02 |
| LOC105379676 | uncharacterized LOC105379676 | 2.14 | 3.39 | 2.4 | 6.06E-05 | 1.04E-02 |
| MIR4522 | microRNA 4522 | 2.29 | 3.57 | 2.4 | 3.58E-02 | 3.09E-01 |
| TMEM171 | transmembrane protein 171 | 4.91 | 6.19 | 2.4 | 3.23E-05 | 7.50E-03 |
| PLD5 | phospholipase D family, member 5 | 4.38 | 5.69 | 2.5 | 5.00E-04 | 3.62E-02 |
| MIR4718 | microRNA 4718 | 1.46 | 2.80 | 2.5 | 1.16E-02 | 1.82E-01 |
| DIAPH3 | diaphanous-related formin 3 | 6.72 | 8.07 | 2.5 | 4.00E-04 | 3.21E-02 |
| LOC105370526 | uncharacterized LOC105370526 | 5.08 | 6.50 | 2.7 | 3.55E-06 | 2.20E-03 |
| MIR1206 | microRNA 1206 | 2.60 | 4.03 | 2.7 | 3.70E-03 | 9.99E-02 |
| SRGN | serglycin | 4.44 | 5.89 | 2.7 | 6.49E-06 | 3.30E-03 |
| CD274 | CD274 molecule | 5.34 | 6.81 | 2.8 | 4.74E-07 | 9.00E-04 |
| ADAMTS6 | ADAM metallopeptidase with thrombospondin type 1 motif 6 | 3.41 | 3.87 | 2.8 | 2.73E-07 | 8.00E-04 |
| ZNF804A | zinc finger protein 804A | 3.18 | 4.66 | 2.8 | 1.00E-04 | 1.40E-02 |

FIG. 12 cont.

| | | | | | |
|---|---|---|---|---|---|
| LOC105375721 | uncharacterized LOC105375721 | 4.37 | 5.88 | 2.9 | 4.62E-05 8.90E-03 |
| MMP1 | matrix metallopeptidase 1 | 6.03 | 7.57 | 2.9 | 7.11E-07 9.00E-04 |
| ANOS1 | anosmin 1 | 4.93 | 6.46 | 2.9 | 7.00E-04 4.09E-02 |
| ZNF875 | zinc finger protein 875 | 1.64 | 3.46 | 3.5 | 5.00E-04 3.47E-02 |
| COL12A1 | collagen, type XII, alpha 1 | 5.14 | 7.15 | 4.0 | 8.59E-05 1.27E-02 |
| IL11 | interleukin 11 | 4.51 | 6.76 | 4.8 | 4.64E-09 7.46E-05 |

FIG. 12 cont.

SUBSTITUTED TETRAHYDROISOQUINOLINES AS ANTI-MITOTIC DRUG IN TRIPLE NEGATIVE BREAST CANCER

CROSS REFERENCE TO RELATED APPLICATIONS

This application is a nonprovisional of and claims priority to U.S. Provisional Patent Application Ser. No. 63/189,475, entitled "Novel Substituted Tetrahydroisoquinolines as Anti-Mitotic Drug in Triple Negative Breast Cancer", filed May 17, 2021, the contents of which are hereby incorporated by reference into this disclosure.

GOVERNMENT SUPPORT

This invention was made with Government support under Grant No. U54 MD007582 awarded by the National Institutes of Health (NIH). The Government has certain rights in the invention.

FIELD OF INVENTION

This invention relates to compounds and methods of treatment for cancer. Specifically, the invention provides novel compounds and methods of treatment for triple negative breast cancer.

BACKGROUND OF THE INVENTION

After lung cancer, breast cancer is the next leading cause of cancer death in women in the United States. In 2020, the American Cancer Society (ACS) reported 281,550 new cases of breast cancer in the in the U.S. and about 43,600 women were expected to die from the disease. Triple-Negative Breast Cancer (TNBC) is the most invasive subtype, and due to lack of hormone receptors is inherently associated with limited treatment option with invasive metastatic disease espousing greater mortality rates in African Americans. While chemotherapy (e.g. use of taxanes and anthracyclines) continues to be the first line treatment of TNBC, many advanced stage patients will succumb to relapse, chemo resistance and mortality.

In light of the limited treatment options for breast cancer, what is needed is a novel breast cancer treatment, particularly TNBC, with limited side effects, lower toxicity to the patient as compared to current therapies, an elevated therapeutic index, and improved patient response rate.

SUMMARY OF INVENTION

Recently, the inventors synthesized and tested a substituted tetrahydroisoquinoline (THIQ) drug molecule (GM-4-53) which is a strong cytostatic agent, comparable to paclitaxel in many aspects, but effective without changing tubulin polymerization/treading retractions, commonly observed in paclitaxel. Additionally, the drug is of smaller molecular weight (MW=296) and greater solubility, and looks to offer multi-target therapeutic advantages over paclitaxel. The drug is novel as is its synthetic scheme and is of a completely different chemical nature from taxanes. The drug has cytostatic drug efficacy compared to paclitaxel and the biochemical attributes of this drug expand beyond mitotic arrest, effects not observed or inherent to paclitaxel, thereby expanding on its drug potential. The data obtained show that both drugs were cytostatic at non-toxic concentrations and caused deformed morphological cytoskeletal enlargement in 2D cultures. In 3D cultures, the data show greater core penetration, observed by GM-4-53, than paclitaxel. In concentrations where the drugs entirely blocked the cell cycle, the transcriptome profile of the 48,226 genes analyzed (selection criteria: (p-value, FDR p-value<0.05, fold change −2< and >2)), paclitaxel evoked 153 differentially expressed genes (DEGs), GM-4-53 evoked 243 DEGs, and, of these changes, 52/153 paclitaxel DEGs were also observed by GM-4-53, constituting a 34% overlap. The 52 DEGS analysis by String database indicates that these changes involve transcripts that influence microtubule spindle formation, chromosome segregation, mitosis/cell cycle, and transforming growth factor-β (TGF-β) signaling. Of interest, both drugs effectively downregulated "inhibitor of DNA binding, dominant negative helix-loop-helix" (ID) transcripts; ID1, ID3 and ID4, and amphiregulin (AREG) and epiregulin (EREG) transcripts, which play a formidable role in cell division. The novel drug may be used as a mainline chemotherapy drug or alternatively as an adjunct to existing standard treatments for triple-negative breast cancer (TNBC) or other cancers due to its solubility, low molecular weight, and capacity to penetrate a small solid tumor mass and effectively block the cell cycle.

In an embodiment, a method of treating cancer in a patient in need thereof is presented comprising administering to the patient in need thereof a therapeutically effective amount of a composition comprising Formula (I)

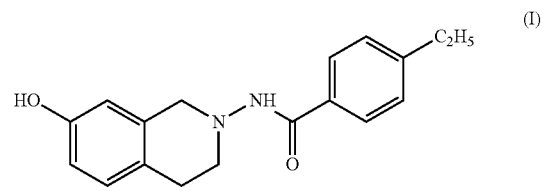 [SMILES: CCc1ccc(C(=O)NN2CCc3ccc(O)cc3C2)cc1]

and a pharmaceutically acceptable carrier.

The cancer may be breast cancer, more particularly triple negative breast cancer (TNBC). After administration expression of several genes such as amphiregulin (AREG), epiregulin (EREG), inhibitor of DNA binding 1 (ID1), inhibitor of DNA binding 3 (ID3), inhibitor of DNA binding 4 (ID4). killer cell lectin like receptor C3 (KLRC3), intercellular adhesion molecule 1 (ICAM-1), and cyclooxygenase-2 (COX2) are downregulated. Oncostatin M(OSM) signaling is also downregulated.

In another embodiment, a method of inhibiting tumor cell proliferation is presented comprising administering to the tumor cells a therapeutically effective amount of a compound comprising Formula (I)

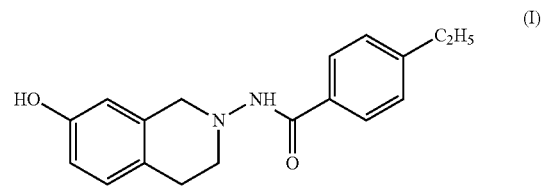 [SMILES: CCc1ccc(C(=O)NN2CCc3ccc(O)cc3C2)cc1]

wherein administration of the compound to the tumor cells inhibits the tumor cell proliferation.

The cancer may be breast cancer, more particularly triple negative breast cancer (TNBC). After administration expression of several genes such as amphiregulin (AREG), epiregulin (EREG), inhibitor of DNA binding 1 (ID1), inhibitor of DNA binding 3 (ID3), inhibitor of DNA binding 4 (ID4), killer cell lectin like receptor C3 (KLRC3), intercellular adhesion molecule 1 (ICAM-1), and cyclooxygenase-2 (COX2) are downregulated. Oncostatin M(OSM) signaling is also downregulated.

BRIEF DESCRIPTION OF THE DRAWINGS

For a fuller understanding of the invention, reference should be made to the following detailed description, taken in connection with the accompanying drawings, in which:

FIG. 1A-B are images depicting (A) novel compound 4-Ethyl-N-(7-hydroxy-3,4-dihydroisoquinolin-2(1H)-yl) benzamide (GM-4-53) having molecular formula $C_{18}H_{20}N_2O_2$ and molecular weight of 296.36; (B) Scheme I for synthesizing GM-4-53. Reaction Conditions: (i) DMF, 0° C., 45 min, (ii) 70% HCl04, p-dioxane, 0° C., 45 min, (iii) 7-Hydroxyisoquinoline, dry $CH_2Cl_2$, $CH_3OH$ (1:1), 0° C., (iv) 4-Ethylbenzoyl Chloride, $Et_3N$, Dry THF, 70° C., (v) $NaBH_4$, abs. EtOH, 7 h.

FIG. 2A-B are a series of graphs depicting cytostatic growth-inhibitory effects of (A) GM-4-53 and (B) paclitaxel over a concentration dose range with end point cell count analysis at day 6 in MDA-MB-231 cells. The data represent cell count/proliferation (as % untreated control) and are expressed as the Mean+S.E.M., with the $IG_{50}$ determined by regression analysis. Significant differences from the control were determined using a one-way ANOVA followed by a Tukey post hoc test. *$p<0.05$.

FIG. 4 is a table depicting variable cell line: cytostatic growth-inhibitory effects of GM-4-53 in Ishikawa, MCF-7 vs. MDA-MB-231 cells were determined by regression analysis. The data show a consistent cytostatic effect in diverse female cancers in the mid-to-high nM range.

FIG. 7 is a table depicting the DEG profile overlap for GM-4-53 and Paclitaxel.

FIG. 8 is an image depicting the functional analysis of the 52 transcripts overlaps in DEGs by paclitaxel and GM-4-53 vs. controls. The data represent significant functional changes as identified by several databases: local network cluster (STRING), Kegg pathways, Reactome Pathways expected protein domains and feature (Interpore), where data are reflected by count in network, strength, and false discovery rates.

FIG. 10 is a table depicting overlapping DEG profiles between GM-4-53 and paclitaxel. The data represent fold change for genes meeting the selection criteria=FC>2 or <−2, p-value<0.05, and FDR p-value<0.05.

FIG. 12 is a table depicting the unique differential effects of GM-4-53.

DETAILED DESCRIPTION OF THE PREFERRED EMBODIMENT

Figure 3:
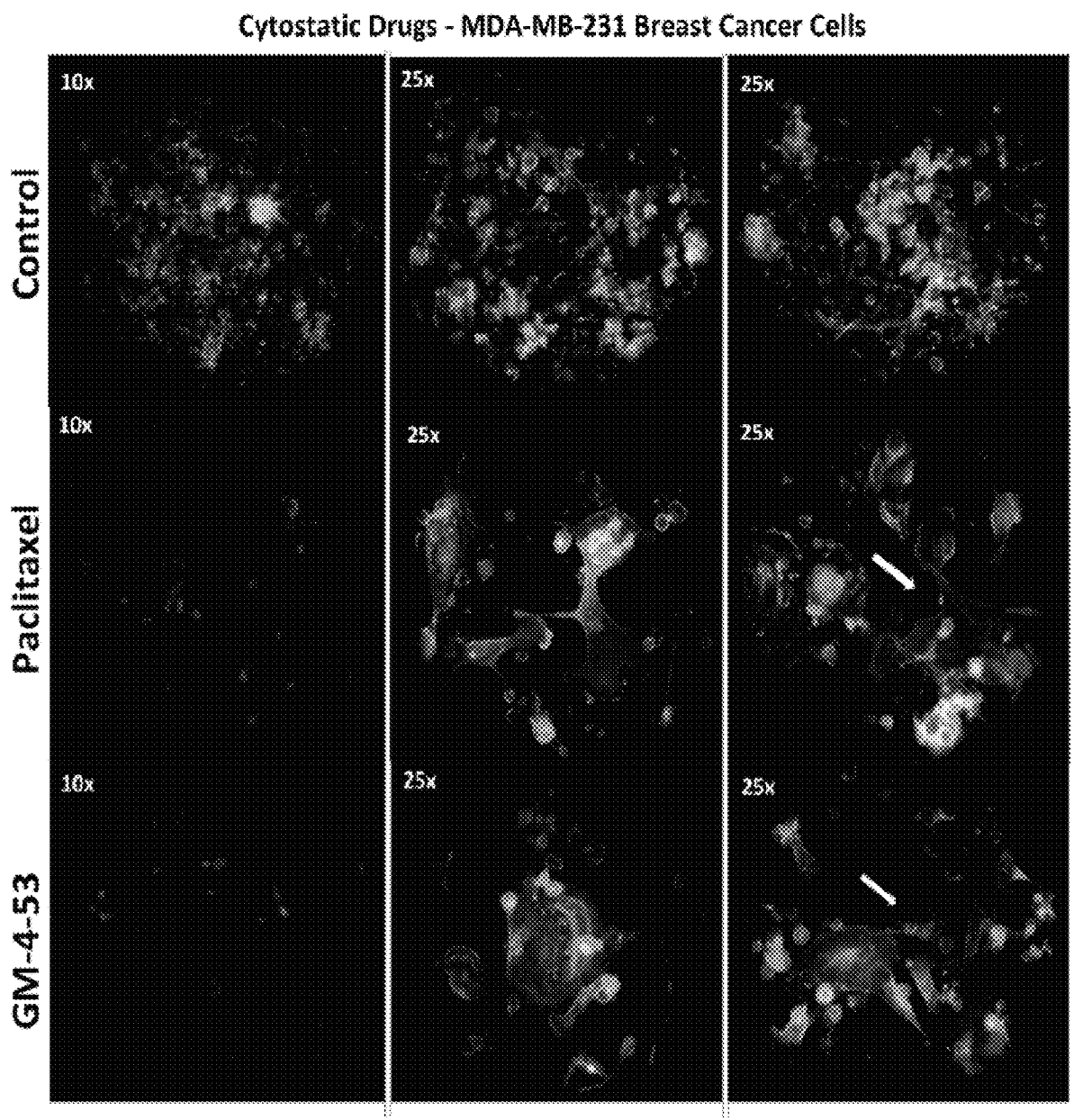
FIG. 3 is a series of images depicting morphological changes associated with cytostatic growth-inhibitory effects by GM-4-53 5 µg/mL and paclitaxel 1 µg/mL in MDA-MB-231 cells evaluated at day 6. The images demonstrate cytostatic changes to the actin cytoskeletal architecture (green) with a propidium iodide nuclear counterstain (red) in the presence of either drug vs. untreated controls. [10×] shows the basic overview of accumulated cell number (cell proliferation), where [25×] shows higher magnification to enable visualization of deformed cell morphology n=2. The images show abnormally large-shaped extended actin networks in cells that are unable to divide.

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Definitions

As used herein, the singular forms "a," "an" and "the" include plural referents unless the context clearly dictates otherwise.

Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

As used herein, "about" means approximately or nearly and in the context of a numerical value or range set forth means±10% of the numerical.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein "patient" is used to describe an animal, preferably a human, to whom treatment is administered, including prophylactic treatment with the compositions of the present invention. "Patient" is used interchangeably with "subject" herein.

As used herein "animal" means a multicellular, eukaryotic organism classified in the kingdom Animalia or Metazoa. The term includes, but is not limited to, mammals. Non-limiting examples include rodents, mammals, aquatic mammals, domestic animals such as dogs and cats, farm animals such as sheep, pigs, cows and horses, and humans. Wherein the terms "animal" or the plural "animals" are used, it is contemplated that it also applies to any animals.

As used herein, the term "pharmaceutically acceptable carrier" is used to describe any of the standard pharmaceutically acceptable carriers. The pharmaceutically acceptable carrier can include excipients such as diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pennsylvania, Mack Publishing Company, 19$^{th}$ ed.) describes formulations which can be used in connection with the subject invention.

Any of the compounds disclosed herein may be administered with or without an excipient. Excipients include, for example, encapsulating materials or additives such as absorption accelerators; antioxidants; binders; buffers; coating agents; coloring agents; diluents; disintegrating agents; emulsifiers; extenders; fillers; flavoring agents; humectants; lubricants; perfumes; preservatives; propellants; releasing agents; sterilizing agents; sweeteners; solubilizers; wetting agents; and mixtures thereof.

As used herein, "administering" or "administration" refers to the process by which the compounds of the present invention are delivered to a subject. The compounds of the present invention may be administered in a variety of ways including, but not limited to, bucally, orally, or parenterally (intramuscularly, intraperitoneally, intrasternally, intraarterially, intravenously, subcutaneously). Any of the compounds may also be delivered through encapsulation in vesicles such as liposomes, niosomes, micelles, etc.

"Treatment" or "treating" as used herein refers to any of: the alleviation, amelioration, elimination and/or stabilization of a symptom or characteristic, as well as delay in progression of a symptom of a particular disorder. For example, "treatment" of cancer may include any one or more of the following: amelioration and/or elimination of one or more symptoms/characteristics associated with cancer, reduction of one or more symptoms/characteristics of cancer, stabilization of symptoms/characteristics of cancer, and delay in progression of one or more symptoms/characteristics of cancer.

As used herein, the term "therapeutically effective amount" is determined based on such considerations as known in the art including the recipient of the treatment, the recipient's tolerance for the compound, the disorder being treated, the severity of the disorder being treated, the composition containing the compound, the time of administration, the route of administration, the duration of treatment, the potency of the compound, the bioavailability of the compound, the rate of clearance of the compound from the body, and whether or not another active agent is co-administered. The amount of the compound of the instant invention that may be administered to a subject must be effective to achieve a response, including but not limited to, improved survival rate, more rapid recovery, and improvement or elimination of symptoms associated with cancers. In accordance with the present invention, a suitable single dose size is a dose that is capable of preventing or alleviating (reducing or eliminating) a symptom in a patient when administered one or more times over a suitable time period. One of ordinary skill in the art can readily determine appropriate single dose sizes for systemic administration based on the size of a mammal and the route of administration.

The term "cancer" as used herein refers to any malignant neoplastic condition involving unregulated cell growth. Non-limiting examples of a cancer that can be treated with the intended use described herein include, but are not limited to, the following: breast cancer including but not limited to triple negative breast cancer, ductal carcinoma, adenocarcinoma, lobular (cancer cell) carcinoma, intraductal carcinoma, medullary breast cancer, mucinous breast cancer, tubular breast cancer, papillary breast cancer, Paget's disease, and inflammatory breast cancer; pancreatic cancer such as, but not limited to, insulinoma, gastrinoma, glucagonoma, vipoma, somatostatin-secreting tumor, and carcinoid or islet cell tumor; leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's lymphoma, non-Hodgkin's lymphoma; multiple myelomas such as but not limited to smoldering multiple myeloma, nonsecretory myeloma, osteosclerotic myeloma, placancer cell leukemia, solitary placancercytoma and extramedullary placancercytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; glial brain tumors (i.e., gliomas) such as but not limited to, astrocytoma, ependymoma, oligodendroglioma, brain stem glioma, optic glioma, diffuse intrinsic pontine glioma, mixed glioma (i.e., oligoastrocytoma), glioblastoma, glioblastoma multiforme, nonglial tumor, acoustic neurinoma, craniopharyngioma, medulloblastoma, meningioma, pineocytoma, pineoblastoma, primary brain lymphoma; adrenal cancer such as but not limited to pheochromocytom and adrenocortical carcinoma; thyroid cancer such as but not limited to papillary or follicular thyroid cancer, medullary thyroid cancer and anaplastic thyroid cancer; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, placancercytoma, verrucous carcinoma, and oat cell (cancer cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America). In some embodiments, the cancer is breast cancer, particularly triple negative breast cancer.

The term "compound" as used herein refers to a chemical formulation, either organic or inorganic, which induces a desired pharmacological and/or physiological effect on a subject when administered in a therapeutically effective amount. "Compound" is used interchangeably herein with "drug" and "therapeutic agent". When the compound name disclosed herein conflicts with the structure depicted, the structure shown will supercede the use of the name to define the compound intended.

As used herein, the term "substituent" means positional variables on the atoms of a core molecule that are attached at a designated atom position, replacing one or more hydrogen atoms on the designated atom, provided that the atom of attachment does not exceed the available valence or shared valence, such that the substitution results in a stable compound. Accordingly, combinations of substituents and/or variables are permissible only if such combinations result in stable compounds. Any carbon atom as well as heteroatom with a valence level that appears to be unsatisfied as described or shown herein is assumed to have a sufficient number of hydrogen atom(s) to satisfy the valences described or shown.

For the purposes of this description, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may be attached more than once on the structure of a core molecule, where the pattern of substitution at each occurrence is independent of the pattern at any other occurrence. Further, the use of a generic substituent variable on a core structure for a compound described herein is understood to include the replacement of the generic substituent with specie substituents that are included within the particular genus, e.g., aryl may be replaced with phenyl or naphthalenyl and the like, such that the resulting compound is to be included within the scope of the compounds described herein.

As used herein, the term "optionally substituted" means that the specified substituent variables, groups, radicals or moieties represent the scope of the genus and may be independently chosen as needed to replace one or more hydrogen atoms on the designated atom of attachment of a core molecule.

As used herein, the terms "stable compound" or "stable structure" mean a compound that is sufficiently robust to be isolated to a useful degree of purity from a reaction mixture and formulations thereof into an efficacious therapeutic agent.

As used herein, the term "form" means a compound of Formula (I) selected from a free acid, free base, salt, ester, hydrate, solvate, chelate, clathrate, polymorph, isotopologue, stereoisomer, racemate, enantiomer, diastereomer, or tautomer thereof.

As used herein, the term "prodrug" means that a functional group on a compound of Formula (I) is in a form (e.g., acting as an active or inactive drug precursor) that is transformed in vivo to yield an active or more active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by V. J. Stella, et. al., "Biotechnology: Pharmaceutical Aspects, Prodrugs: Challenges and Rewards," American Association of Pharmaceutical Scientists and Springer Press, 2007.

The compounds of Formula (I) or a form thereof can form salts, which are intended to be included within the scope of this description. Reference to a compound of Formula (I) or a form thereof herein is understood to include reference to salts thereof, unless otherwise indicated. The term "salt(s)", as employed herein, denotes acidic salts formed with inorganic and/or organic acids, as well as basic salts formed with inorganic and/or organic bases.

The term "pharmaceutically acceptable salt(s)", as used herein, means those salts of compounds of Formula (I) or a form thereof described herein that are safe and effective (i.e., non-toxic, physiologically acceptable) for use in mammals and that possess biological activity, although other salts are also useful. All such acid salts and base salts are intended to be included within the scope of pharmaceutically acceptable salts as described herein. In addition, all such acid and base salts are considered equivalent to the free forms of the corresponding compounds for purposes of this description.

The use of the terms "salt," "solvate," "ester," "prodrug" and the like, is intended to apply equally to the salt, solvate, ester and prodrug of enantiomers, stereoisomers, rotamers, tautomers, positional isomers, racemates, isotopologues or prodrugs of the instant compounds.

Unless otherwise stated, structures depicted herein are also meant to include all isomeric (e.g., enantiomeric, diastereomeric, optical, and geometric (or conformational)) forms of the structure or a form thereof (including salts, solvates, esters, and prodrugs and transformed prodrugs thereof); for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms.

The compounds of Formula (I) or a form thereof described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds of Formula (I) or a form thereof described herein are (S) isomers and may exist as enantiomerically pure compositions substantially comprising only the (S) isomer. In another embodiment, the compounds of Formula (I) or a form thereof described herein are (R) isomers and may exist as enantiomerically pure compositions substantially comprising only the (R) isomer. As one of skill in the art will recognize, when more than one chiral center is present, the compounds of Formula (I) or a form thereof described herein may also exist as a (R,R), (R,S), (S,R) or (S,S) isomer, as defined by IUPAC Nomenclature Recommendations.

As used herein, the term "substantially pure" refers to compounds of Formula (I) or a form thereof consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

As used herein, the term "racemate" refers to any mixture of isometric forms that are not "enantiomerically pure", including mixtures such as, without limitation, in a ratio of about 50/50, about 60/40, about 70/30, or about 80/20, about 85/15 or about 90/10.

All stereoisomers (for example, geometric isomers, optical isomers and the like) of the present compounds of Formula (I) or a form thereof (including salts, solvates, esters and prodrugs and transformed prodrugs thereof), which may exist due to asymmetric carbons on various substituents, including enantiomeric forms (which may exist even in the absence of asymmetric carbons), rotameric forms, atropisomers, diastereomeric and regioisomeric forms, are contemplated within the scope of the description herein. Individual stereoisomers of the compounds of Formula (I) or a form thereof described herein may, for example, be substantially free of other isomers, or may be present in a racemic mixture, as described supra.

The term "isotopologue" refers to isotopically-enriched compounds of Formula (I) or a form thereof which are identical to those recited herein, but for the fact that one or more atoms are replaced by an atom having an atomic mass or mass number different from the atomic mass or mass number usually found in nature.

One or more compounds of Formula (I) or a form thereof described herein may exist in unsolvated as well as solvated forms with pharmaceutically acceptable solvents such as water, ethanol, and the like, and the description herein is intended to embrace both solvated and unsolvated forms As used herein, the term "solvate" means a physical association of a compound of Formula (I) or a form thereof described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates.

Polymorphic crystalline and amorphous forms of the compounds of Formula (I) or a form thereof, and of the salts, solvates, esters and prodrugs of the compounds of Formula (I) or a form thereof, are further intended to be included in the scope of the compounds of Formula (I) or a form thereof described herein.

Also falling within the scope described herein are the in vivo metabolic products of the compounds of Formula (I) or a form thereof. Such products may result, for example, from the oxidation, reduction, hydrolysis, amidation, glucuronidation, esterification and the like of the administered compound of Formula (I) or a form thereof, primarily due to enzymatic processes. Accordingly, the compounds of Formula (I) or a form thereof described herein include those produced by a process comprising contacting a compound of Formula (I) or a form thereof described herein with a mammalian tissue or a mammal for a period of time sufficient to yield a metabolic product thereof.

Breast Cancer

After lung cancer, breast cancer is the second leading cause of cancer death in women in the United States. In 2020, the American Cancer Society (ACS) reported 281,550 new cases of breast cancer in the in the U.S. and about 43,600 women were expected to die from the disease[1]. Breast cancer incidence among Black women is lower than among white women, but the mortality rate is higher in among Black women. Triple Negative Breast Cancer (TNBC) is characterized by a lack of Estrogen Receptors (ER), Progesterone Receptors (PR) and Human Epidermal Growth Factor Receptor 2 (HER2) being invasive, it is one of the most aggressive forms of breast cancer worsened by limited treatment options (to the exclusion of hormone based chemotherapies) and is associated with higher mortality in African Americans[2,3]. TNBC is commonly associated with advanced stage diagnosis, shorter disease-free survival, and a proclivity toward distant bone metastasis than non-TNBC breast cancers[2,4]. Currently, standard treatments for TNBC include combination use of taxanes (docetaxel and paclitaxel), anthracyclines (doxorubicin and epirubicin), cyclophosphamide, fluorouracil, capecitabine, or platinum-based drugs[5,6].

The broad pathophysiology of breast cancers involves underlying genetic defects having been well established for diverse oncogenes involved with tumor initiation (MYC, ERBB2 CCND1[7,8], tumor progression (FOS, JUNB)[9], proliferation and metastasis (EGRF)[10,11] and loss of tumor suppressor functional genes TP53 and E-cadherin[7,12], compounded by defects in DNA repair systems (MDM2, PTEN, RB1 and BRCA1/2 genes)[13-15]. The TNBC sub-class is further defined by genetic changes accounting for epithelial-to-mesenchymal transition (EMT), rampant cell proliferation (CDKN1A, PI3K/Akt Wnt/beta-catenin signaling, nitric oxide, collagen/cytokeratin synthesis), and stem cell differentiation (S-100, p63, or vimentin), superimposed on epigenetic gains and losses[16-21]. Once TNBC is treated by chemotherapy or radiation, the treatment alone accounts for additional genetic changes where resistance and aggressive malignancy is brought about by an upregulation of genes associated with immune evasion (PTGS2, IL-6, CCL2, CXCL8, and CXCL 12)[22,23], angiogenesis (ANGPT1, VEG FA), advanced and rapid cell cycle progression (EGR1, MYC, FOS, CDKN1A, CA2, ANKRD46) and multidrug resistance[16,22,24-26].

Given that TNBC mortality rates affect African Americans to greater extent, this continues to remain a public health concern, and new drug therapies must continually be explored. The tetrahydroisoquinoline (THIQ) core structure is an important pharmacophore in natural products and small molecules that are active drug molecules. The THIQ moieties were reported to be selective estrogen receptor modulators (SERMs) and microtubule disruptors and possess potent cytotoxic activities such as antitumor and antimicrobial activities[27, 28]. Recently, the inventors synthesized a substituted tetrahydroisoquinoline molecule (GM-4-53) (FIG. 1A), which appears to be a strong cytostatic agent, when compared to paclitaxel, without changing tubulin polymerization/treading retractions common to the latter[29,30]. In comparing this novel drug against paclitaxel in TNBC by whole transcriptomic analysis, one can clearly see overlapping similarity of these drugs, and unique additional attributes specific to each.

In brief, the inventors found that out of 48,226 genes analyzed, paclitaxel elicited differential gene expression (OGE) for 153 transcripts, GM-4-53 elicited DEGs for 243 genes; there was an overlap between the GM-4-53 and paclitaxel for 52 DEGs in magnitude (fold change) and direction. Both tested compounds downregulated genes involved with Erb/TGF-beta signaling, mitotic cytokinesis, G2/M phase replication, complement activation, and carbonic anhydrase. Given the excellent solubility of GM-4-53, its low molecular weight, and dynamic capacity to halt the cell cycle and at the same time offer multi-target effects to thwart metastasis and stem cell survival, it can be indicated that GM-4-53 has a good potential for main-line TNBC therapy.

Materials and Methods

Hanks balanced salt solution (HBSS), [4-(2-hydroxyethyl)-1-piperazine-ethanesulfonic acid] (HEPES), ethanol, cell culture 24-well plates, 96-well plates, flasks, paclitaxel, general reagents, and supplies were purchased from Sigma-Aldrich Co. (St. Louis, MO, USA) and VWR International (Radnor, PA, USA).

Chemistry

Synthesis and characterization of tetrahydroisoquinoline GM-4-53 was reported previously[30,31] and shown in Scheme 1 as depicted in FIG. 1B. O-mesitylene sulfonyl hydroxylamine (MSH) was used to prepare the N-amino salt as an aminating agent, as previously reported[32]. To an ice-cooled solution of 7-hydroxy isoquinoline (5) (20.67 mmol) in anhydrous methylene chloride and anhydrous methanol (1:1) (60 ml) was added MSH (4) (22.74 mmol) in dry methylene chloride (10 ml) over 5 min with stirring. The reaction was stirred at 0° C. for 6 h, at which time ether (80 ml) was added and the suspension was filtered. The precipitate was recrystallized from ethyl acetate-methanol (5:1 v/v) to give N-amino-7-hydroxy isoquinolinium-2,4,6-trimethyl-benzenesulfonate salt (6) in high yield. To an ice-cold solution of (6) (4.16 mmol) in anhydrous tetrahydrofuran (40 ml), containing triethylamine (2.0 ml) were added 4-ethyl benzoylchloride (7) (8.32 mmol). The mixture was allowed to proceed for 12 h at 70° C. After the completion of the reaction (monitored by TLC), it was quenched by adding 30 ml of saturated aqueous sodium bicarbonate solution. Extraction with dichloromethane (3 ml×100 ml), drying over anhydrous sodium sulfate and removal of the solvent in vacuo gave the crude product, which was purified on CombiFlash chromatography using ethyl acetate: hexane (3:2 v/v) mixture as eluent. The Ylide, N-(4-ethylbenzoyl)-7-hydroxyisoquinolin-2-ium-2-aminide (8) were obtained in fair to good yields. The Ylide (8) (5 mmol) was dissolved in absolute ethanol (20 ml) and added dropwise to a solution of sodium borohydride (50 mmol) in absolute ethanol (25 ml) at 0° C. The reaction was allowed to proceed for 5 h to 7 h. Water (35 ml) was added and allowed to warm up to room temperature. Extraction with dichloromethane (3 ml×50 ml), drying over anhydrous sodium sulfate and removal of the solvent in vacuo gave the crude product which was purified on CombiFlash chromatography using ethyl acetate:hexane (3:2 v/v) as eluent to afford pure compound 4-Ethyl-N-(7-hydroxy-3,4-dihydroisoquinolin-2(1H)-yl)benzamide (GM-4-53) in 65% yield.

Cell Culture

MDA-MB-231 cells (ATCC® HTB-26™) were used. These cells are human triple negative breast cancer cells, which we obtained from American Type Culture Collection (ATCC) (Manassas, VA, USA). MDA-MB-231 cells were initially brought up in ATCC-formulated Leibowitz's L-15 medium, supplemented with 10% fetal bovine serum (FBS) and penicillin/streptomycin (100 U/0.1 mg/ml). After confluence, the cells were sub-cultured and grown in Dulbecco's modified Eagle's medium (DMEM) containing phenol red, 7.5% FBS, 4 mM L-glutamine, 20 µM sodium pyruvate, and penicillin/streptomycin (100 U/0.1 mg/ml). Cells were maintained at 37° C. in 5% CO2/atmosphere, and every 2-5 days, the medium was replaced and cells sub-cultured. The growth medium was used for all experiments conducted herein.

The anti-proliferative activity of GM-4-53 on two additional cell lines was evaluated at the Southern Research Institute (SRI, Birmingham, Alabama, USA). There, the human MCF-7 breast cancer cell line was purchased from the NCI. The human Ishikawa endometrial cancer cell line was purchased from Sigma Aldrich. Both cell lines were cultured in phenol red-free RPMI-1640 (Hyclone) (500 mL), supplemented with L-glutamine-dipeptide (Hyclone) (5 mL), and 10% fetal bovine serum (Atlanta Biologicals) (50 mL).

Proliferation and Cell Viability Studies

For MDA-MB-231 cells, both paclitaxel and GM-4-53 were dissolved in DMSO and stored at 20° C. A stock solution for both compounds was prepped in HBSS. In brief, 96-well plates were seeded with cells ($0.04 \times 10^5$/well) to a volume of 200 µL, to which drugs were added, and cell proliferation (as cell count) was evaluated at a 6-day endpoint, using Alamar blue. For Alamar blue testing, a working solution of resazurin prepared in sterile phosphate-buffered saline (PBS)-phenol red (0.5 mg/mL) was added (15% v/v) to each sample in a 96-well plate. Samples were returned to the incubator for 4-6 h, and the reduction in the dye (to resorufin, a fluorescent compound) caused by viable cells was quantitatively analyzed using a Synergy HTX multimode reader (Bio-Tek, Winooski, VT, USA), with excitation/emission wavelength settings at 550 nm/580 nm. Cell count was evaluated as % control, and the inhibitory growth ($IG_{50}$) value was calculated by regression analysis. Cytotoxicity studies were carried out at equal dose concentrations as proliferation studies at a higher plating density ($0.5 \times 10^5$/well), over 24-36 h. The cytostatic effects of MCF-7 and Ishikawa cell lines were determined using the CellTiter-Glo (CTG) cell viability assay, which is based on the direct determination of intracellular ATP level (determining the number of viable cells in culture based on the quantification of ATP present), which signals the presence of metabolically active cells. Luminescence results were read on TriLux Luminometer. Optimal concentrations for microarray were established by a lack of cell toxicity, at a concentration showing a complete blockage of cell proliferation; paclitaxel (1 µg/mL) and GM-4-53 (5 µg/mL). For microarray studies, cells were plated and treated in 75 cm3 flasks for 36 h.

3D Tumor Studies

MDA-MB-231 cells were plated in low-adhesion, round-bottom, sterile, 96-well plates at a cell density of ($0.2 \times 10^5$/well), in 200 uL of cell culture media centrifuged at 1800×g for 3 min prior to incubation at 37° C. in 5% C02/atmosphere. For the first 3 days, cells were taken out and re-centrifuged at 1800×g×3 min. 3D spheroids were left to grow for 10 days. On day 14, experimental drugs were added, and images were captured on day 24.

Imaging 2D cell cultures were imaged to ascertain changes in morphological structure at the 6-day endpoint in MDA-MB-231 cells in the presence or absence of treatments. In brief, cells were fixed in 4% paraformaldehyde and incubated at 37° C. in 5% $CO_2$/atmosphere for 15 min. After delicate removal of paraformaldehyde, sterile ultra-pure biological grade water containing 0.2% Triton X-100 was gently added to each well (100 uL) and returned to the incubator for 45 min. After gentle removal, a PBS solution containing propidium iodide (1 µg/mL) and Phalloidin-iFluor 488 Reagent (ab176753) was added to each well, according to the manufacturer's instructions Abcam (Cambridge, MA, USA), and images were captured on an inverted fluorescent microscope using the 10× and 25× fluo-objectives. 3D tumors were stained with fluorescein diacetate (live-cell dye) and countered imaged for morphology.

Microarray WT 2.1 Human Datasets

After the experimental 36-hour time point, the cells were scraped, washed three times in ice-cold HBSS, spun down, the supernatant removed, and the remaining pellet was rapidly frozen and stored at –80° C. Total RNA was isolated and purified using the Trizol/chloroform method. The RNA quality was assessed, and concentrations were equalized to 82 ng/µl in nuclease-free water. According to the GeneChip™ WT PLUS Reagent Manual for Whole Transcript (WT) expression arrays, whole transcriptome analysis was conducted. Briefly, RNA was reverse transcribed to first strand/second strand cRNA. The cRNA was purified and assessed for yield before the second cycle single-stranded cDNA synthesis, hydrolysis of RNA, and purification of the second cycle single-stranded cDNA. Subsequently, cDNA was assessed for yield, fragmented, labeled, and hybridized onto the arrays before being subjected to fluidics and imaging using the Gene Atlas (Affymetrix, ThermoFisher Scientific). The array data, quality control, and initial processing from CEL to CHP files were conducted using an expression console before data evaluation using the Affymetrix transcriptome analysis console (Wiki/Kegg pathways) and protein-protein interaction (PPI) String Database (String Consortium 2020)[1]. The dataset has been deposited to NIH Gene Expression OmniBus.

Data Analysis

Statistical analysis was performed using Graph Pad Prism (version 3.0; Graph Pad Software Inc. San Diego, CA, USA). The significance of the difference between groups assessed using a one-way ANOVA, followed by Tukey post hoc means comparison test or Student's t-test. $IG_{50}$ were determined by regression analysis using Origin Software (Originlab, Northampton, MA, USA).

Results

The anti-proliferative $IG_{50}$ growth inhibitory concentrations was established in a prolonged 6-day growth study for GM-4-53 (FIG. 2A) and paclitaxel (FIG. 2B). The $IG_{50}$ for paclitaxel was 9.6 nM, and GM-4-53 was 261 nM. To establish that cell toxicity was not an interfering variable, the inventors conducted a 36-hour toxicity assay at equal drug concentrations in high plating density $0.5 \times 10^5$ cells/well (data not shown), where no cytotoxic effects were found. Optimal concentrations used for whole transcriptomic (WT) microarray analysis were selected as 1 µg/ml for paclitaxel, and 5 g/ml for GM-4-53, to establish a complete cell cycle blockade without cytotoxic effects, and a 36 hour time point was chosen for endpoint analysis to elucidate changes at the gene transcript levels.

The altered cytoskeletal changes evident at the 6-day endpoint are reflected in FIG. 3, stained with phalloidin (actin) and propidium iodide (nuclear counterstain) in fixed permeabilized cells. The 10× images reflect the proliferation rate vs. controls, corresponding to the data in FIG. 2A, B, where the 25× images show a zoom in on the gross abnormalities in cytoskeletal architecture evoked by both cytostatic agents. Furthermore, cell proliferation using comparative human female cancer cell lines was carried out by the Southern Research Institute, where the $IG_{50}$s are presented in FIG. 4, showing efficacy in the mid-to-high nM range by GM-4-53 in diverse female cancer cell lines.

Figure 5:
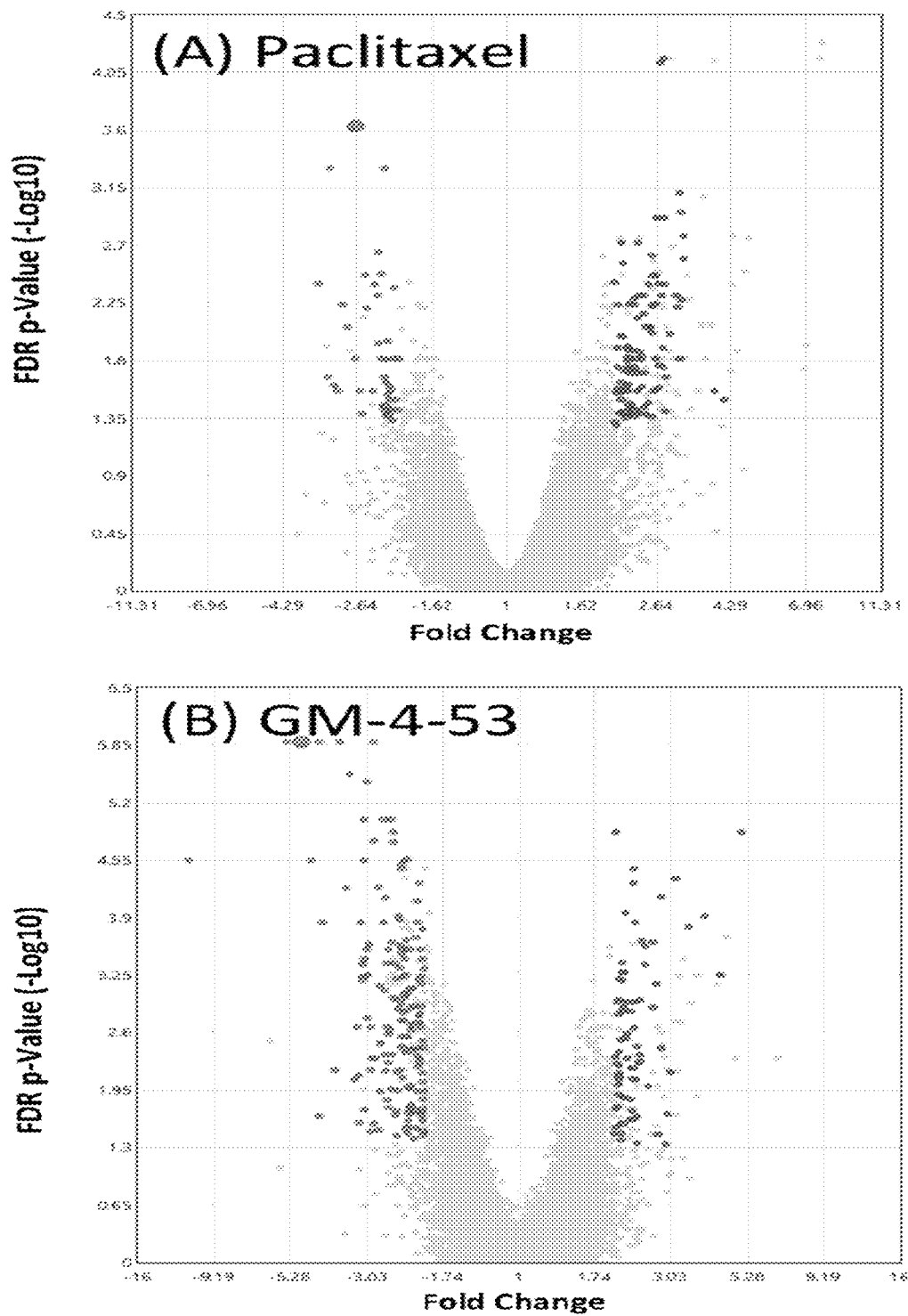
FIG. 5A-B is a series of images depicting a summary of gene changes by fold change and significance in cytostatic cells vs. untreated controls from a total of 48,226 genes analyzed. (A) paclitaxel (1 µg/mL) vs. controls (B) GM 4-53 (5 µg/mL) in MDA-MB-231. The data show upregulated DEGs (right/green) and downregulated DEGs (left/red) by fold change relative to untreated controls (X-axis), with FDR p-values (Y-axis). Selected criteria for array analysis: Fold change >2 or <−2, p-value<0.05, and false discovery rate (FDR) p-value<0.05. Plotted points denoted in gray did not meet the selected criteria.
Figure 6:
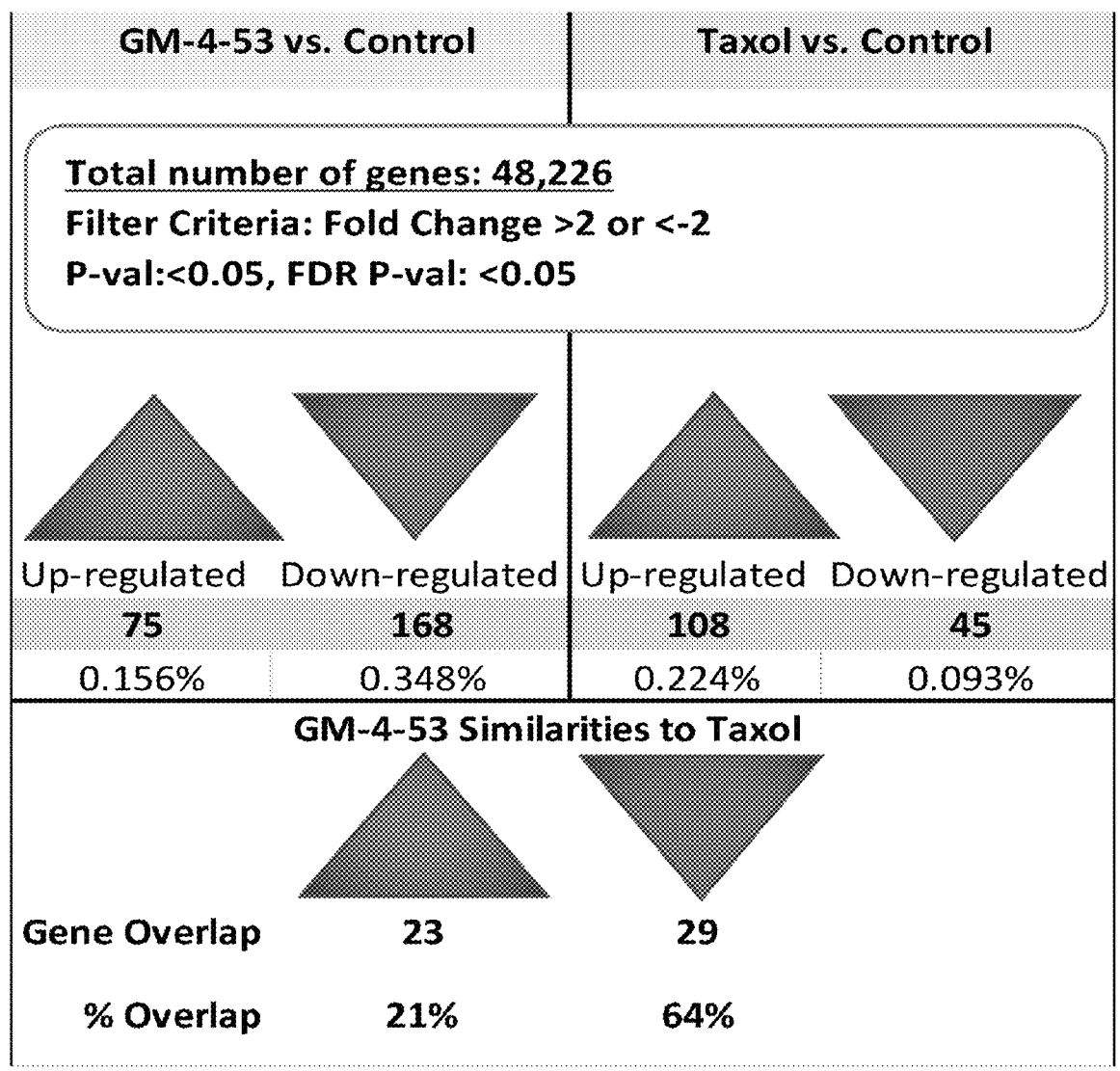
FIG. 6 is an image depicting the Gene Summary Report. Overall summary of DEGs reflected by whole-transcriptomic analysis in GM-4-53 (5 µg/mL)- or Paclitaxel (1 µg/mL)-treated cells vs. controls after 36 h of incubation in MDA-MB-231 cells; Criteria=FC>2 or <−2, p-Value<0.05 and FDR p-value<0.05. Information on overlapping DEGs common to paclitaxel and GM-4-53 are also displayed.

A summary view of significant transcriptomic differentially expressed genes (DEGs) by both compounds is presented in FIG. 5 according to fold change and significance (volcano plot). Specifics of these gene changes are shown in FIG. 6 where out of 48,226 transcripts tested, approximately 99.4% of the transcriptome remained unaffected. The FIG. 6 summary shows that GM-4-53 evoke 75 upregulated DEGs vs. controls, 168 down-regulated DEGs vs. controls; paclitaxel evoked 108 upregulated DEGS vs. controls and 45 down-regulated DEGs vs. controls, with 52 of these genes being shared by both drugs. Of the 45 genes down-regulated by paclitaxel, 29 of these were also observed by GM-4-53, which constitutes a 64% overlap. This appears as a fingerprint profile showing a near identical pattern of influence in both directions, with pronounced effects of GM-4-53 (over paclitaxel) on 101, KLRC3, CSF1, and 103. The full data on both individual drug effects and overlapping DEGS is presented in FIG. 7 as gene symbol, gene description, average Log2 (signals) fold change (FC), P-Value, and false discovery rate (FDR).

Figure 9:
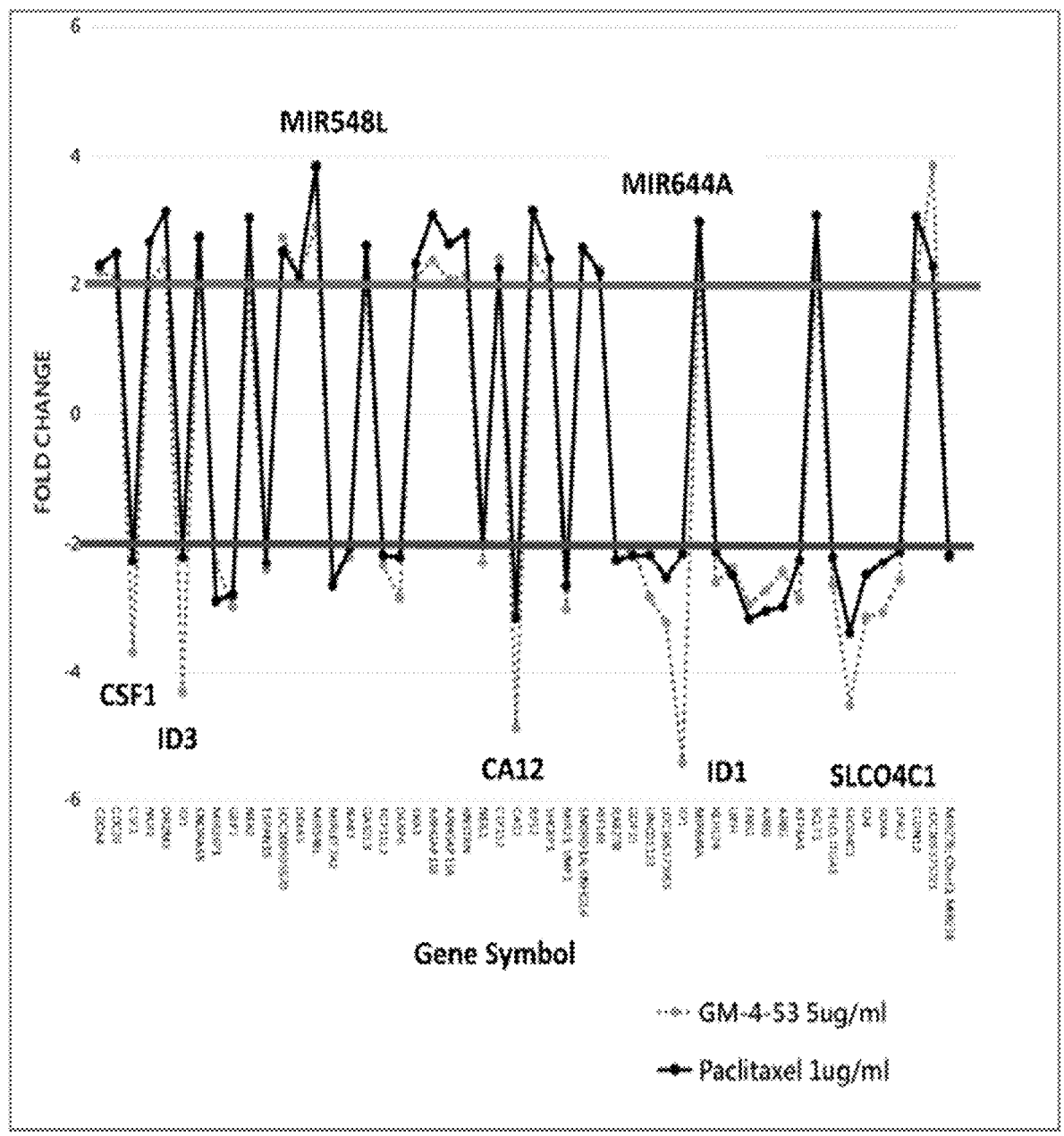
FIG. 9 is an image depicting overlapping DEG profile between GM-4-53 and paclitaxel. The data represent fold change for genes meeting the selection criteria=FC>2 or <−2, p-value<0.05, and FDR p-value<0.05.
Figure 11:
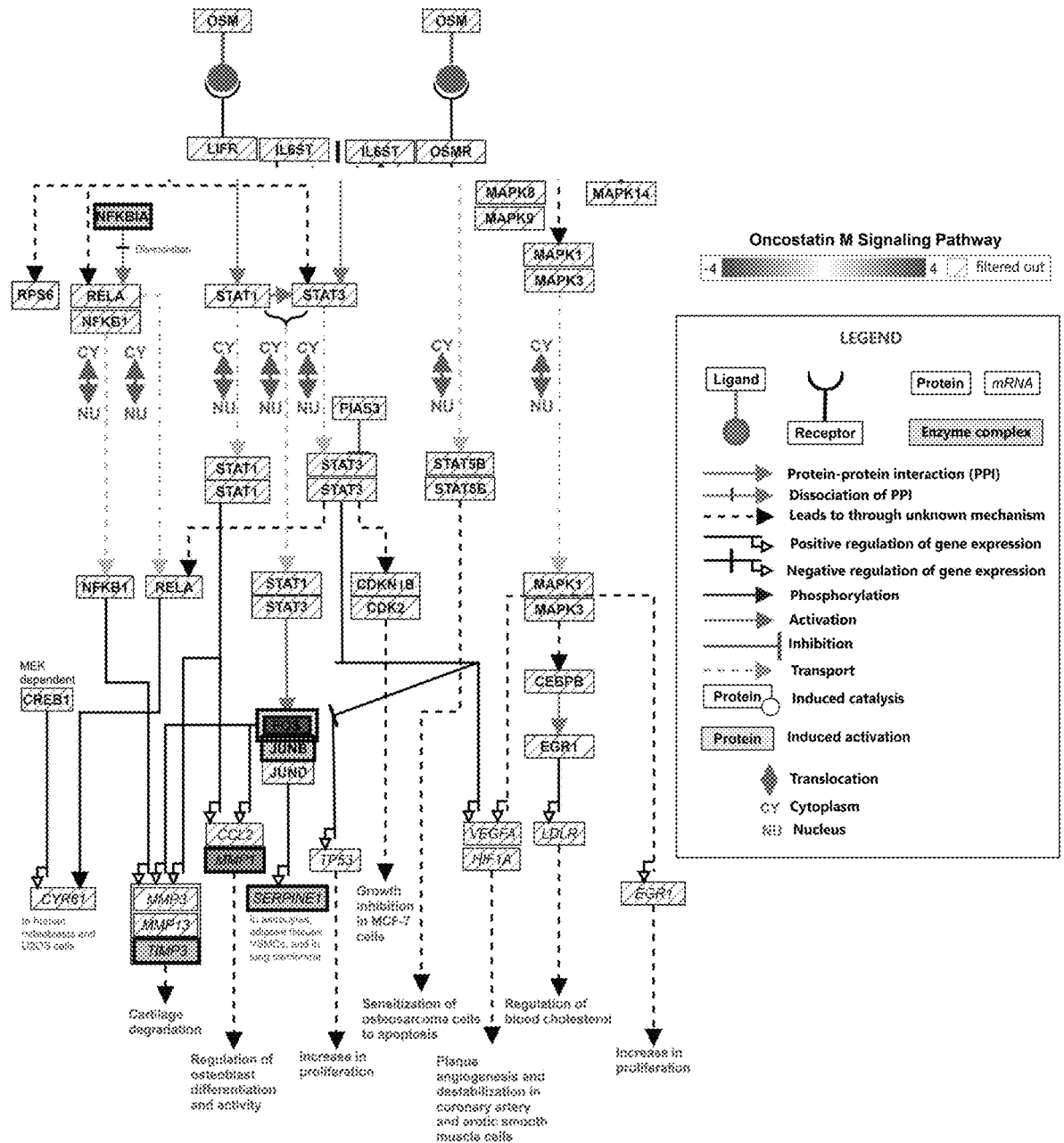
FIG. 11 is an image depicting the effect of GM-4-53 on the Oncostatin M Signaling pathway relative to Untreated Controls. Downregulated DEGs (red color intensity) and upregulated DEGs (green color intensity) are displayed on the pathway elements, being significantly different from untreated controls.

Using STRING/Protein-Protein Functional Enrichment Analysis, the inventors examined this gene overlap as shown in FIG. 8. The data show both drug target genes having a primary molecular classification impact on spindle microtubules, chromosomal segregation, spindle microtubules to the kinetochore, TGF-β signaling, and the MAPK signaling pathway. The 52-gene overlap, using a plotted fold overlay (FIG. 9), shows the magnitude (FC) and direction (up/down) of these particular DEGs to be closely aligned; some of these are listed in the table of FIG. 10. The most significantly affected systems include: cytokinesis (G2/M), DNA replication, and Epidermal (EGF) TGF-beta signaling, complement activation, and carbonic anhydrases. Affymetrix Transcriptome Analysis Console was used to further evaluate the most significant pathway for GM-4-53 relative to untreated controls, which was the Oncostatin M Signaling Pathway (FIG. 11).

Figure 13:
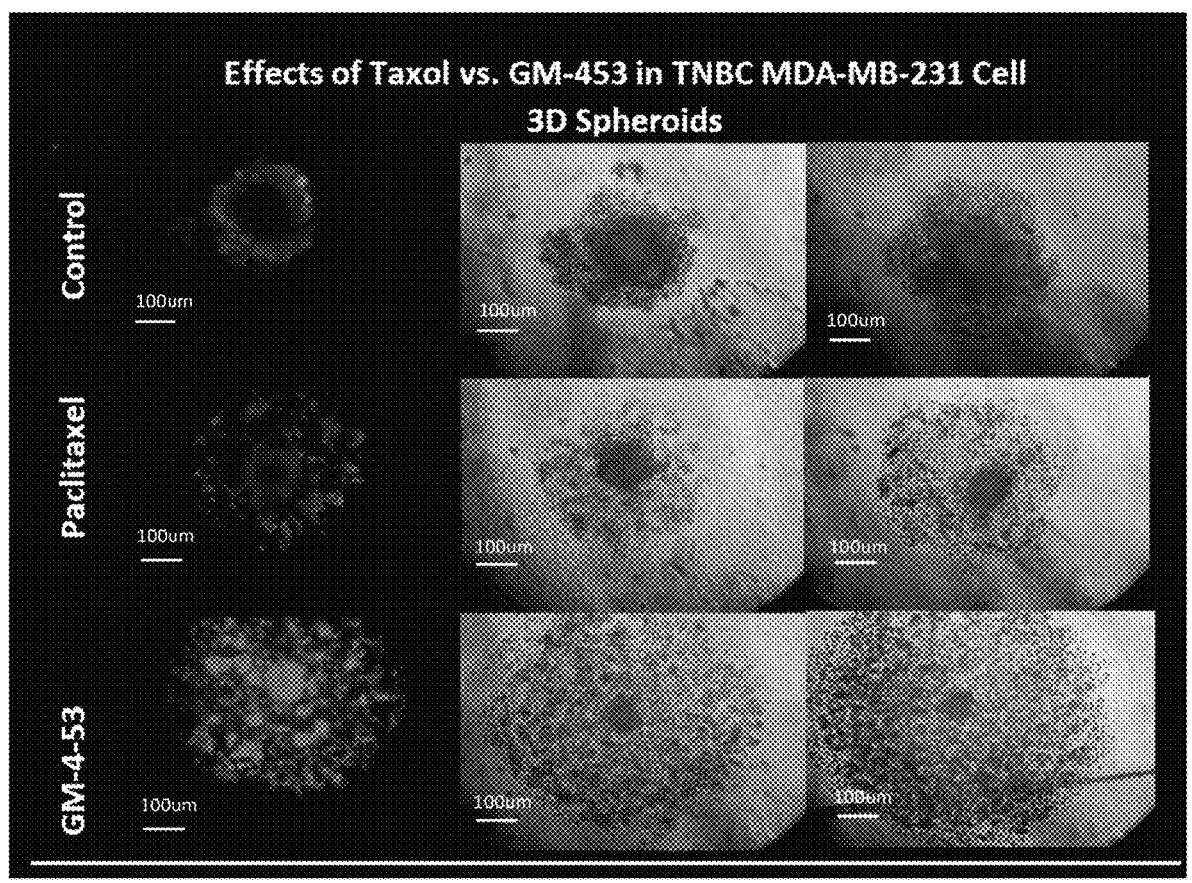
FIG. 13 is a series of images depicting the effect of GM-4-53 (5 µg/mL) and paclitaxel (1 µg/mL) on 3D tumors. The left panel represents cell viability (fluorescein diacetate), and the right 2 panels show basic cell morphology (n=2).

The comparable efficacy of the two drugs in 3D tumor models was also established (FIG. 13). Although a dose-response was carried out, a consistent morphological pattern of grossly distorted cytostatic cells was observed throughout all effective doses tested, as shown in FIG. 2. The data in FIG. 13 show a very distinct and unusual pattern between the two drugs, where paclitaxel appears to halt the growth of the spheroid and central core, whereas GM-4-53 halts the growth and appears to penetrate the tumor core, leading to mass dispersion of viable cytostatic cells.

The inventors evaluated the effects of a novel synthetic compound GM-4-53 vs. a standard control drug (paclitaxel) on transcriptomic pattern in TNBC cells known to lack estrogen and progesterone receptors (ER/PR) and HER2. There is no doubt that GM-4-53 has many anticancer effects in common with paclitaxel, as both are cytostatic drugs, which fully block the cell cycle at non-cytotoxic concentrations, and evoke massive changes in the cytoskeletal architecture, disrupting microtubule dynamics and inducing cell-cycle arrest. Microtubule dynamics disrupters are mainline cancer drugs, as they can block the normal equilibrium, which allows cell structures to expand, retract, change shape, divide, and move. Cytostatic compounds such as paclitaxel are a front-line treatment in many cancers because they impair the dynamics of cytoskeletal fluidity in cancer cells, paralyzing microtubules (stabilized) by either blocking tubulin depolymerization or polymerization (destabilized), meaning that cell division is no longer possible[88,89]. This can occur via two basic classes of drugs (1) (e.g., taxanes, epothilones, cyclosstreptin, steroids, lactones, and natural compounds), referred to as microtubules stabilizing agents (MSA)s, which block tubulin depolymerization, or (2) drugs that inhibit polymerization of tubulin (destabilizing agents) (MDAs) such as colchicine, vinblastine and combretastatin-A4[90]. MDAs and MSAs block cell-cycle progression holding the filaments static, thereby preventing chromosome attachment/segregation and spindle formation required for mitotic cell division[91,92]. The limitations to using these drugs to treat cancer, as is the case for paclitaxel, include inherent side effects, chemoresistance, and poor aqueous solubility, with limited access to the blood-brain barrier.[93,94]

Drug therapeutic failures are ultimately responsible for mortality rates. As a result, there is a continuous demand for safe and efficient alternatives to TNBC cytostatic drugs, which may work through a different mechanism, enabling improved antitumor response and patient outcome. After our lab revealed GM-4-53 to be a potent cytostatic agent, the first obvious target evaluated was its effect on the tubulin polymerization/depolymerization processes; where the data failed to show any effect and showed only mild effects on the process of tubulin nucleation, suggesting there must be additional mechanisms in play. Interestingly, while the effects of paclitaxel are not believed to involve a mechanism of action occurring at the gene level, the findings in this work were not expected, showing that many elements of the cell cycle are altered at the transcriptome level. It was also surprising to find significant overlap in the transcriptome in response to paclitaxel and GM-4-53, particularly in down-regulated transcripts require for cell cycle and mitosis. Secondly, the data show DEG shifts that are unique to paclitaxel, which is reportedly observed to be associated with taxol chemoresistance, such as upregulated transcription of kinesin super-family members, spindle assembly processes (e.g., MAD2, KIF11 (also known as kinesin-5 and Eg5), centrosomal proteins, centromere proteins, cell-division-cycle-associated genes, cyclins, centrioles, and aurora A, some of which also amplify chromosomal and spindle processes in paclitaxel refractory cancers.[95-98]

Information from whole-transcriptomic analysis on the effects of paclitaxel discussed herein provides information on changes that could align with drug resistance. While paclitaxel has been rigorously studied for decades, there is no known information on GM-4-53 or how it mediates its effect on cell division. For this reason, the inventors searched for DEG overlaps in common to both drugs.

Both drugs caused a pronounced downregulation of "inhibitor of DNA Binding/Inhibitor of differentiation" (ID) transcripts for ID1, ID3, and ID4, with GM-4-53 having more significant effects than paclitaxel. IDs are implicated in the control of cell division and mitosis not only during embryonic development but also in numerous cancers, including TNBC, being linked to larger tumor size, advanced histological grade, metastasis, vascular invasion, stem cell phenotype, lymph node invasion, and poor clinical outcomes. The ID genes may control cell division by the indirect regulation of processes involving CDKN1A (p21) and CDKN1B (p27)[77]. In TNBC and other cancers, the ID oncogenic transcripts foster diverse cancer-related events, including EMT, signaling (e.g., EGFR/TGF-β, K-Ras, WNT, STAT3, PI3K/Akt, OCT-4/ID1/NF-x(3), where ID genes are a target of many anticancer drugs, including vinblastine.[78-83] Drugs such as GM-4-53 that can downregulate IDs are believed to offer therapeutic roles in the attenuation of TNBC progression and other cancers, with a capacity to offset chemoresistance associated with various drugs.[84-86] Regarding the impact of down-regulated ID transcripts by both paclitaxel and GM-4-53, these are known to play a direct role in impeding cell division. Several studies seem to suggest that ID1 exerts control over cell cycle and self-renewal capacity of TNBC in vitro and in vivo, with its absence (silencing) leading to G0/G1 cell cycle arrest.

Regarding the commonalities of both cytostatic drugs, both paclitaxel and GM-4-53 significantly downregulated amphiregulin (AREG) and epiregulin (EREG) mRNA, which while required for breast luminal development (by EGF binding/activating EGFR (ERBB)), if overexpressed, is associated with aggressive breast cancers of diverse type (ER+erb2, HER2 and TNBC)[35-39]. AREG/EREGs also play a critical role in fibrotic processes and development of cancer-associated fibroblasts (CAFS), thereby playing a role in both the cancer and the conducive tumor microenvironment (TME) required for rapid tumor growth[40-43].

Briefly, AREG/EREG ectodomain ligands are shed into exosomes by tumor necrosis factor-alpha converting enzyme (TACE/ADAM17), as fully competent ligands which then bind/activate tumor EGFR (ErbB1-4) receptors and trigger oncogenic signaling: (phosphatidylinositol 3-kinase/Akt, Ras/Raf/MEK/ERK1/2 and phospholipase C) cell proliferation, and release of cytokines that accelerated leukocyte infiltration to the tumor microenvironment (TME) and immune escape[44,45]. The intra-cellular product (pro-AREG) enters into the nucleus, turning on oncogenes[46-49]. This mechanism is highly relevant in diverse cancers as EGFT ligand/receptors are targeted with current chemotherapies[50] such as (Cetuximab Pertuzumab, Trastuzumab) ligand binders or drugs that interact with the receptor (Gefitinib, Erlotinib, and Lapatinib)[5]. Drugs like GM-4-53 that interfere with AREG in particular for chemo resistant breast cancers or TNBC cell models should in theory acquiesce tumor growth, TAM infiltration[52], and block activation of diverse EGF receptors (ErbB1,3 & 4+ErbB2 HER2/Neu)[53-56].

A secondary attribute of GM-4-53, apart from paclitaxel involves its control over oncostatin M (OSM) signaling, which plays a role in propelling metastatic breast cancer by co-harboring with EREG in exosomes[57]. The inventors also show GM-4-53 to invoke a general loss of oncogenic transcription factors (FOS, JUN-b, and NFKB1a) that drives OSM signaling, where this pathway plays a critical role in driving advanced invasive TNBCss[8]. OSM can be released by the cancer cell itself, acting also as a chemokine in driving tumor-associated macrophages (TAMS), and CAFS, all of which collectively work to degrade the tumor microenvironmental (TME) matrix and enable a 2-way trafficking system. That two-way traffic includes [toward the tumor] via OSM mediated M2 polarized macrophages[59,60] and leukocytes; whereas [away from the tumor] occurs via OSM mediated metastatic dissociation, heightened levels of circulating tumor cells and a then reseed of stem cells into secondary metastatic site locations[61,62].

The effects of OSM on osteolytic bone destruction enable stem cells to harbor in a dormant latent haven[63], while at the same time causing de-differentiation of TNBC cells into highly aggressive cancer stem cell state (tumor sphere formation, migratory capacity)[64]. Meanwhile, at the primary tumor site, OSM can signal elements required for tumor survival and growth[61] by halting apoptotic processes and assisting in EMT plasticity[65,66]. OSM is likely to be one of the most potent cytokines involved with breast cancers responsible for mesenchymal/stem cell transition and signaling in tumor cells, including activation of JAK1/STAT3/MYC[67,68] and Ras/Raf/MAPK/ERK[69]. Novel drugs such as GM-4-53 that can down-regulate OSM signaling could be a targeted therapeutics for TNBC[58], enabling more significant clinical outcomes[70,72] and potentially reducing bone and lymph node metastasis[63].

As an added benefit of both drugs, paclitaxel, and GM-4-53 both reduced the expression of ICAM-1, which is a known element involved with cell migration via docking and trafficking of leukocytes toward cancer and stromal cells. These events lead to the loss of immune surveillance[73,74].

Several other genes influenced by both drugs, but to a greater extent in GM-4-53 include the loss of the KLRC3 transcript, an otherwise potent gene driving rampant tumor cell proliferation, metastatic invasion, and the ultimate creation of chemo and radiation-resistant cancers[75,76] most notable albeit in glioblastoma[75].

Lastly, both drugs GM-4-53 and paclitaxel, also downregulated the expression of COX2, which plays a formidable role in inflammatory breast cancer as well as serving as a cancer biomarker in TNBC[87]. The data herein clearly show that GM-4-53 is a cytostatic, non-cytotoxic agent with a similar effect on TNBC to the mainline drug, paclitaxel. The lack of cytotoxicity by paclitaxel has been observed in ex vivo explants of human breast tumors, which penetrate a tumor and disrupt mitosis without directly invoking cytotoxicity. There is a clear distinction between cytotoxic drugs vs. cytostatic drugs, demarcated by the extremely large difference in drug dose concentrations between lower-dose effective blocks on cell proliferation ($IG_{50}$) vs. cell viability ratios ($IC_{50}$), where dead cells do not divide. While the inventors show that both drugs affect established 3D spheroid tumors, GM-453 appears to have significant effects on the clustering of cells or penetration of the tumor spheroid, which could theoretically either prevent tumor formation and/or alter the metastatic proclivity of circulating tumor cells.

The following non-limiting example illustrates exemplary compounds and methods thereof in accordance with various embodiments of the disclosure. The example is merely illustrative and are not intended to limit the disclosure in any way.

Example 1—Treatment of TNBC with 4-Ethyl-N-(7-hydroxy-3,4-dihydroisoquinolin-2(1H)-yl) benzamide (GM-4-53)

A 35 year old Black female patient presents with a lump in her left breast. A biopsy of the mass is performed and the cells are found to lack estrogen or progesterone receptors and HER2 protein thus confirming a diagnosis of triple negative breast cancer (TNBC). The patient is administered a therapeutically effective amount of 4-Ethyl-N-(7-hydroxy-3,4-dihydroisoquinolin-2(1H)-yl) benzamide (GM-4-53) for a time period sufficient to inhibit cell proliferation. The patient is tested at regular intervals while the drug is being administered as well as after administration has stopped. The patient is deemed in remission.

CONCLUSION

As in the case of GM-4-53, there are several areas of potential targeted chemotherapy influence on the transcriptome relating to TNBC breast cancers, which at the basic minimum involves the following; 1) anti-mitotic (blocking cancer cell division) 2) anti-stromal/fibrotic 3) anti-TAM recruitment 4) anticancer stem cell and 5) antimetastatic.

GM-4-53 has a good potential for TNBC therapy, given the excellent solubility of GM-4-53, its low molecular weight, ability to penetrate a small solid tumor mass and effectively block its cell cycle while at the same time offer multi-target effects to thwart metastasis and stem cell survival.

REFERENCES

1. Siegel, R. L., Miller, K. D., Fuchs, H. E., Jemal, A. American Cancer Society: Cancer Facts & FIGS. 2021. CA Cancer Journal for Clinicians, 2021, 71: 7-33.
2. Vidal G, Bursae Z, Miranda-Carboni G, White-Means S, Starlard-Davenport A. Racial disparities in survival outcomes by breast tumor subtype among African American women in Memphis, Tennessee. Cancer Med 2017; 6(7), 1776-86.
3. Sturtz L A, Melley J, Mamula K, Shriver C D, Ellsworth R E. Outcome disparities in African American women with triple negative breast cancer: a comparison of epidemiological and molecular factors between African American and Caucasian women with triple negative breast cancer. BMC Cancer 2014, 14, 62.
4. Sakhuja S, Deveaux A, Wilson L E, Vin-Raviv N, Zhang D, Braithwaite D, et al. Patterns of de-novo metastasis and breast cancer-specific mortality by race and molecular subtype in the SEER population-based dataset. Breast Cancer Res Treat 2020.
5. Verma S, Provencher L, Dent R. Emerging trends in the treatment of triple-negative breast cancer in Canada: a survey. Curr Oncol 2011; 18(4):180-90.
6. Lorusso V, Latorre A, Giotta F. Chemotherapy Options beyond the First Line in HER Negative Metastatic Breast Cancer. J Oncol 2020; 2020:9645294
7. Ingvarsson S. Molecular genetics of breast cancer progression. Semin Cancer Biol 1999; 9(4):277-88.
8. Cline M J, Battifora H, Yokota J. Proto-oncogene abnormalities in human breast cancer: correlations with anatomic features and clinical course of disease. J Clin Oncol 1987; 5(7):999-1006.
9. Ping Z, Xia Y, Shen T, Parekh V, Siegal G P, Eltoum I E, et al. A microscopic landscape of the invasive breast cancer genome. Sci Rep 2016; 6:27545.
10. Yang D C, Elliott R L, Head J F. Gene targets of antisense therapies in breast cancer. Expert Opin Ther Targets 2002; 6(3):375-85.
11. Wang S, Li X, Zhang W, Gao Y, Zhang K, Hao Q, et al. Genome-Wide Investigation of Genes Regulated by ER-alpha in Breast Cancer Cells. Molecules 2018; 23(10).
12. Shabnaz S, Ahmed M U, Islam M S, Islam M R, AI-Mamun M M, Islam M S, et al. Breast cancer risk in relation to TP53 codon 72 and CDH1 gene polymorphisms in the Bangladeshi women. Tumour Biol 2016; 37(6):7229-37.
13. Bareche Y, Venet D, lgnatiadis M, Aftimos P, Piccart M, Rothe F, et al. Unravelling triple negative breast cancer molecular heterogeneity using an integrative multiomic analysis. Ann Oncol 2018; 29(4):895-902.
14. Muendlein A, Rohde B H, Gasser K, Haid A, Rauch S, Kinz E, et al. Evaluation of BRCA1/2 mutational status among German and Austrian women with triple-negative breast cancer. J Cancer Res Clin Oncol 2015; 141(11): 2005-12.
15. Palomba G, Budroni M, Olmeo N, Atzori F, lonta M T, Pisano M, et al. Triple-negative breast cancer frequency and type of BRCA mutation: Clues from Sardinia. Oncol Lett 2014; 7(4):948-52.
16. Zhou Z R, Wang X Y, Yu X L, Mei X, Chen X X, Hu Q C, et al. Building radiation-resistant model in triple-negative breast cancer to screen radio resistance-related molecular markers. Ann Transl Med 2020; 8(4):108.
17. Li M, Li H, Liu F, Bi R, Tu X, Chen L, et al. Characterization of ovarian clear cell carcinoma using target drug-based molecular biomarkers: implications for personalized cancer therapy. J Ovarian Res 2017; 10(1):9.
18. Reddy T P, Rosato R R, Li X, Moulder S, Piwnica-Worms H, Chang J C. A comprehensive overview of metaplastic breast cancer: clinical features and molecular aberrations. Breast Cancer Res 2020; 22(1):121.
19. Chen J, Liu C, Cen J, Liang T, Xue J, Zeng H, et al. KEGG-expressed genes and pathways in triple negative breast cancer: Protocol for a systematic review and data mining. Medicine (Baltimore) 2020; 99(18): e 19986.
20. Shome R, Ghosh S S. Tweaking EMT and MDR dynamics to constrain triple-negative breast cancer invasiveness by EGFR and Wnt/beta-catenin signaling regulation. Cell Oncol (Dordr) 2021.
21. Ring A, Kaur P, Lang J E. EP300 knockdown reduces cancer stem cell phenotype, tumor growth and metastasis in triple negative breast cancer. BMC Cancer 2020; 20(1): 1076.
22. Jurj A, Pop L A, Zanoaga O, Ciocan-Cartita C A, Cojocneanu R, Moldovan C, et al. New Insights in Gene Expression Alteration as Effect of Paclitaxel Drug Resistance in Triple Negative Breast Cancer Cells. Cell Physiol Biochem 2020; 54(4):648-64.
23. Zhu C, Ge C, He J, Zhang X, Feng G, Fan S. Identification of Key Genes and Pathways Associated With Irradiation in Breast Cancer Tissue and Breast Cancer Cell Lines. Dose Response 2020; 18(2).
24. Marczyk M, Patwardhan G A, Zhao J, Qu R, Li X, Wali V B, et al. Multi-Omics Investigation of Innate Navitoclax Resistance in Triple-Negative Breast Cancer Cells. Cancers (Basel) 2020; 12(9).
25. Li W, You Y, Zhang X, Song Y, Xiang H, Peng X, et al. Amplification of chromosome 8q21-qter associated with the acquired paclitaxel resistance of nasopharyngeal carcinoma cells. Int J Clin Exp Pathol 2015; 8(10):12346-56.
26. Loftus P G, Watson L, Deedigan L M, Camarillo-Retamosa E, Dwyer R M, O'Flynn L, et al. Targeting stromal cell Syndecan-2 reduces breast tumour growth, metastasis and limits immune evasion. Int J Cancer 2021; 148(5): 1245-59.
27. Jordan V C. Chemoprevention of breast cancer with selective o-estrogen-receptor modulators. Nat Rev Cancer 2007; 7(1):46-53.
28. Maximov P Y, Lee T M, Jordan V C. The discovery and development of selective estrogen receptor modulators (SERMs) for clinical practice. Curr Clin Pharmacol 2013; 8(2):135-55.
29. Gangapuram M, Jean R, Mazzio E, Badisa R, Eyunni S, Goodman C B, et al. Substituted Tetrahydroisoquinolines as Microtubule-destabilizing Agents in Triple Negative Human Breast Cancer Cells. Anticancer Res 2016; 36(10):5043-52.
30. Eyunni S V K, Gangapuram M, Mochona B, Mateeva N, Redda K K, J Cancer Sci Ther. 2017, 9(7): 528-540.
31. Kinfe Ken Redda and Madhavi Gangapuram, "N-Substituted Tetrahydroisoquinoline benzamides/benzene Sulfonamides as Anticancer Agents", U.S. Pat. No. 8,889, 713 81, issued on Nov. 18, 2014.
32. Tamura Y., et al., A novel method for heteroaromatic N-amines. J. Org Chem. 1972, 40:4133-4135.
33. Szklarczyk D, Franceschini A, Kuhn M, Simonovic M, Roth A, Minguez P, et al. The STRING database in 2011: functional interaction networks of proteins, globally integrated and scored. Nucleic Acids Res 2011; 39(Database issue):D561-8.
34. Szklarczyk D, Gable A L, Nastou K C, Lyon D, Kirsch R, Pyysalo S, et al. The STRING database in 2021:

35. Mukhopadhyay C, Zhao X, Maroni D, Band V, Naramura M. Distinct effects of EGFR ligands on human mammary epithelial cell differentiation. PLoS One 2013; 8(10):e75907.
36. Olsen D A, Bechmann T, Ostergaard B, Warnberg P A, Jakobsen E H, Brandslund I. Increased concentrations of growth factors and activation of the EGFR system in breast cancer. Clin Chem Lab Med 2012; 50(10):1809-18.
37. Peterson E A, Jenkins E C, Lofgren K A, Chandiramani N, Liu H, Aranda E, et al. Amphiregulin Is a Critical Downstream Effector of Estrogen Signaling in ERalpha-Positive Breast Cancer. Cancer Res 2015; 75(22):4830-8.
38. Schmucker H, Blanding W M, Mook J M, Wade J F, Park J P, Kwist K, et al. Amphiregulin regulates proliferation and migration of HER2-positive breast cancer cells. Cell Oncol (Dordr) 2018; 41 (2):159-68.
39. 35. Williams C B, Soloff A C, Ethier S P, Yeh E S. Perspectives on Epidermal Growth Factor Receptor Regulation in Triple-Negative Breast Cancer: Ligand-Mediated Mechanisms of Receptor Regulation and Potential for Clinical Targeting. Adv Cancer Res 2015; 127: 253-81.
40. Kefaloyianni E, Keerthi Raja M R, Schumacher J, Muthu M L, Krishnadoss V, Waikar S S, et al. Proximal Tubule-Derived Amphiregulin Amplifies and Integrates Profibrotic EGF Receptor Signals in Kidney Fibrosis. J Am Soc Nephrol 2019; 30(12):2370-83.
41. Wang Y, Jing Y, Ding L, Zhang X, Song Y, Chen S, et al. Epiregulin reprograms cancer associated fibroblasts and facilitates oral squamous cell carcinoma invasion via JAK2-STAT3 pathway. J Exp Clin Cancer Res 2019; 38(1):274.
42. Rajaram M, Li J, Egeblad M, Powers R S. System-wide analysis reveals a complex network of tumor-fibroblast interactions involved in tumorigenicity. PLoS Genet 2013; 9(9):e1003789.
43. Xiang G, Liu F, Liu J, Meng Q, Li N, Niu Y. Prognostic role of Amphiregulin and the correlation with androgen receptor in invasive breast cancer. Pathol Res Pract 2019; 215(6):152414.
44. Higginbotham J N, Demory Beckler M, Gephart J D, Franklin J L, Bogatcheva G, Kremers G J, et al. Amphiregulin exosomes increase cancer cell invasion. Curr Biol 2011; 21 (9):779-86.
45. Roskoski R, Jr. The ErbB/HER family of protein-tyrosine kinases and cancer. Pharmacol Res 2014; 79:34-74.
46. Tanaka H, Nishioka Y, Yokoyama Y, Higashiyama S, Matsuura N, Matsuura S, et al. Nuclear envelope-localized EGF family protein amphiregulin activates breast cancer cell migration in an EGF-like domain independent manner. Biochem Biophys Res Commun 2012; 420(4): 721-6.
47. Rego S L, Helms R S, Dreau D. Tumor necrosis factor-alpha-converting enzyme activities and tumor-associated macrophages in breast cancer. Immunol Res 2014; 58(1):87-100.
48. Taverna S, Pucci M, Giallombardo M, Di Bella M A, Santarpia M, Reclusa P, et al. Amphiregulin contained in NSCLC-exosomes induces osteoclast differentiation through the activation of EGFR pathway. Sci Rep 2017; 7(1):3170.
49. Kim J W, Kim D K, Min A, Lee K H, Nam H J, Kim J H, et al. Amphiregulin confers trastuzumab resistance via AKT and ERK activation in HER2-positive breast cancer. J Cancer Res Clin Oncol 2016; 142(1):157-65.
50. Revillion F, Lhotellier V, Hornez L, Bonneterre J, Peyrat J P. ErbB/HER ligands in human breast cancer, and relationships with their receptors, the bio-pathological features and prognosis. Ann Oncol 2008; 19(1):73-80.
51. Katoh Y, Katoh M. Canonical WNT signaling pathway and human AREG. Int J Mol Med 2006; 17(6):1163-6.
52. Nickerson N K, Mill C P, Wu H J, Riese D J, 2nd, Foley J. Autocrine-derived epidermal growth factor receptor ligands contribute to recruitment of tumor-associated macrophage and growth of basal breast cancer cells in vivo. Oncol Res 2013; 20(7):303-17.
53. Riese D J, 2nd, Cullum R L. Epiregulin: roles in normal physiology and cancer. Semin Cell Dev Biol 2014; 28:49-56.
54. Xia Q, Zhou Y, Yong H, Wang X, Zhao W, Ding G, et al. Elevated epiregulin expression predicts poor prognosis in gastric cancer. Pathol Res Pract 2019; 215(5):873-9.
55. He M, Jin Q, Chen C, Liu Y, Ye X, Jiang Y, et al. The miR-186-3p/EREG axis orchestrates tamoxifen resistance and aerobic glycolysis in breast cancer cells. Oncogene 2019; 38(28):5551-65.
56. Liu S, Wang Y, Han Y, Xia W, Zhang L, Xu S, et al. EREG-driven oncogenesis of Head and Neck Squamous Cell Carcinoma exhibits higher sensitivity to Erlotinib therapy. Theranostics 2020; 10(23):10589-605.
57. Vlaicu P, Mertins P, Mayr T, Widschwendter P, Ataseven B, Hogel B, et al. Monocytes/macrophages support mammary tumor invasivity by co-secreting lineage-specific EGFR ligands and a STAT3 activator. BMC Cancer 2013; 13:197.
58. Nguyen T N, Rajapakshe K, Nicholas C, Tordesillas L, Ehli E A, Davis C M, et al. Integrative transcriptomic analysis for linking acute stress responses to squamous cell carcinoma development. Sci Rep 2020; 10(1):17209.
59. Shrivastava R, Asif M, Singh V, Dubey P, Ahmad Malik S, Lone M U, et al. M2 polarization of macrophages by Oncostatin M in hypoxic tumor microenvironment is mediated by mTORC2 and promotes tumor growth and metastasis. Cytokine 2019; 118:130-43.
60. Tripathi C, Tewari B N, Kanchan R K, Baghel K S, Nautiyal N, Shrivastava R, et al. Macrophages are recruited to hypoxic tumor areas and acquire a pro-angiogenic M2-polarized phenotype via hypoxic cancer cell derived cytokines Oncostatin M and Eotaxin. Oncotarget 2014; 5(14):5350-68.
61. Masjedi A, Hajizadeh F, Beigi Dargani F, Beyzai B, Aksoun M, Hojjat-Farsangi M, et al. Oncostatin M: A mysterious cytokine in cancers. Int Immunopharmacol 2020:107158.
62. Tawara K, Bolin C, Koncinsky J, Kadaba S, Covert H, Sutherland C, et al. OSM potentiates pre-intravasation events, increases CTC counts, and promotes breast cancer metastasis to the lung. Breast Cancer Res 2018; 20(1):53.
63. Omokehinde T, Johnson R W. GP130 Cytokines in Breast Cancer and Bone. Cancers (Basel) 2020; 12(2).
64. Doherty M R, Parvani J G, Tamagno I, Junk D J, Bryson B L, Cheon H J, et al. The opposing effects of interferon-beta and oncostatin-M as regulators of cancer stem cell plasticity in triple-negative breast cancer. Breast Cancer Res 2019; 21 (1):54.
65. Nguyen A M, Zhou J, Sicairos B, Sonney S, Du Y. Upregulation of CD73 Confers Acquired Radioresistance and is Required for Maintaining Irradiation-selected Pancreatic Cancer Cells in a Mesenchymal State. Mol Cell Proteomics 2020; 19(2):375-89.

66. Browning L, Patel M R, Horvath E B, Tawara K, Jorcyk C L. IL-6 and ovarian cancer: inflammatory cytokines in promotion of metastasis. Cancer Manag Res 2018; 10:6685-93.
67. Junk D J, Bryson B L, Smigiel J M, Parameswaran N, Bartel C A, Jackson M W. Oncostatin M promotes cancer cell plasticity through cooperative STAT3-SMAD3 signaling. Oncogene 2017; 36(28):4001-13.
68. Bryson B L, Junk D J, Cipriano R, Jackson M W. STAT3-mediated SMAD3 activation underlies Oncostatin M-induced Senescence. Cell Cycle 2017; 16(4):319-34.
69. Litherland G J, Elias M S, Hui W, Macdonald C D, Catterall J B, Barter M J, et al. Protein kinase C isoforms zeta and iota mediate collagenase expression and cartilage destruction via STAT3- and ERK-dependent c-fos induction. J Biol Chem 2010; 285(29):22414-25.
70. Sterbova S, Karlsson T, Persson E. Oncostatin M induces tumorigenic properties in non-transformed human prostate epithelial cells, in part through activation of signal transducer and activator of transcription 3 (STAT3). Biochem Biophys Res Commun 2018; 498(4):769-74.
71. Parashar D, Geethadevi A, Aure M R, Mishra J, George J, Chen C, et al. miRNA551 b-3p Activates an Oncostatin Signaling Module for the Progression of Triple-Negative Breast Cancer. Cell Rep 2019; 29(13):4389-406.
72. Shien K, Papadimitrakopoulou V A, Ruder D, Behrens C, Shen L, Kalhor N, et al. JAK1/STAT3 Activation through a Proinflammatory Cytokine Pathway Leads to Resistance to Molecularly Targeted Therapy in Non-Small Cell Lung Cancer. Mol Cancer Ther 2017; 16(10): 2234-45.
73. West N R. Coordination of Immune-Stroma Crosstalk by IL-6 Family Cytokines. Front Immunol 2019; 10:1093.
74. Peng Z P, Jiang Z Z, Guo H F, Zhou M M, Huang Y F, Ning W R, et al. Glycolytic activation of monocytes regulates the accumulation and function of neutrophils in human hepatocellular carcinoma. J Hepatol 2020; 73(4): 906-17.
75. Cheray M, Bessette B, Lacroix A, Melin C, Jawhari S, Pinet S, et al. KLRC3, a Natural Killer receptor gene, is a key factor involved in glioblastoma tumourigenesis and aggressiveness. J Cell Mol Med 2017; 21(2):244-53.
76. Park H, Ohshima K, Nojima S, Tahara S, Kurashige M, Hori Y, et al. Adenylosuccinate lyase enhances aggressiveness of endometrial cancer by increasing killer cell lectin-like receptor C3 expression by fumarate. Lab Invest 2018; 98(4):449-61.
77. Sharma P, Patel D, Chaudhary J. ld1 and ld3 expression is associated with increasing grade of prostate cancer: ld3 preferentially regulates CDKN1B. Cancer Med 2012; 1(2):187-97.
78. Thankamony A P, Murali R, Karthikeyan N, Varghese B A, Teo W S, McFarland A, et al. Targeting the ld1-Kif11 Axis in Triple-Negative Breast Cancer Using Combination Therapy. Biomolecules 2020; 10(9).
79. Teo W S, Holliday H, Karthikeyan N, Cazet A S, Roden D L, Harvey K, et al. Id Proteins Promote a Cancer Stem Cell Phenotype in Mouse Models of Triple Negative Breast Cancer via Negative Regulation of Robol. Front Cell Dev Biol 2020; 8:552.
80. Tasdemir N, Ding K, Savariau L, Levine K M, Du T, Elangovan A, et al. Proteomic and transcriptomic profiling identifies mediators of anchorage-independent growth and roles of inhibitor of differentiation proteins in invasive lobular carcinoma. Sci Rep 2020; 10(1):11487.
81. Wahdan-Aswad R, Harrell J C, Fan Z, Edgerton S M, Liu B, Thor A D. Metformin attenuates transforming growth factor beta (TGF-beta) mediated oncogenesis in mesenchymal stemlike/claudin-low triple negative breast cancer. Cell Cycle 2016; 15(8): 1046-59.
82. Castanon E, Bosch-Barrera J, Lopez I, Collado V, Moreno M, Lopez-Picazo J M, et al. ld1 and ld3 co-expression correlates with clinical outcome in stage III-N2 non-small cell lung cancer patients treated with definitive chemoradiotherapy. J Transl Med 2013; 11:13.
83. Chen Y H, Wu Z Q, Zhao Y L, Si Y L, Guo M Z, Han W D. FHL2 inhibits the ld3-promoted proliferation and invasive growth of human MCF-7 breast cancer cells. Chin Med J (Engl) 2012; 125(13):2329-33.
84. O'Brien C A, Kreso A, Ryan P, Hermans K G, Gibson L, Wang Y, et al. ID1 and ID3 regulate the self-renewal capacity of human colon cancer-initiating cells through p21. Cancer Cell 2012; 21 (6):777-92.
85. Yang H Y, Liu H L, Liu G Y, Zhu H, Meng Q W, Qu L D, et al. Expression and prognostic values of ld-1 and ld-3 in gastric adenocarcinoma. J Surg Res 2011; 167(2):258-66.
86. Shuno Y, Tsuno N H, Okaji Y, Tsuchiya T, Sakurai D, Nishikawa T, et al. ld1/ld3 knockdown inhibits metastatic potential of pancreatic cancer. J Surg Res 2010; 161 (1):76-82.
87. Basudhar D, Bharadwaj G, Somasundaram V, Cheng RYS, Ridnour L A, Fujita M, et al. Understanding the tumour micro-environment communication network from an NOS2/COX2 perspective. Br J Pharmacol 2019; 176 (2): 155-76.
88. Castle, B. T.; McCubbin, S.; Prahl, L. S.; Bernens, J. N.; Sept, D.; Odde, D. J. Mechanisms of kinetic stabilization by the drugs paclitaxel and vinblastine. Mol. Biol. Cell 2017, 28, 1238-1257.
89. Shi, X.; Sun, X. Regulation of paclitaxel activity by microtubule-associated proteins in cancer chemotherapy. Cancer Chemother. Pharmacol. 2017, 80, 909-917.
90. Naaz, F.; Haider, M. R.; Shafi, S.; Yar, M. S. Anti-tubulin agents of natural origin: Targeting taxol, vinca, and colchicine binding domains. Eur. J. Med. Chem. 2019, 171, 310-331.
91. Leung, J. C.; Cassimeris, L. Reorganization of paclitaxel-stabilized microtubule arrays at mitotic entry: Roles of depolymerizing kinesins and severing proteins. Cancer Biol. Ther. 2019, 20, 1337-1347.
92. Bai, Z.; Liu, X.; Guan, Q.; Ding, N.; Wei, Q.; Tong, B.; Zhao, M.; Zhang, W.; Ma, L. 5-(3,4,5-trimethoxybenzoyl)-4-methyl-2-(p-tolyl) imidazole (BZML) targets tubulin and DNA to induce anticancer activity and overcome multidrug resistance in colorectal cancer cells. Chem. Biol. Interact. 2020, 315, 108886.
93. Xie, S.; Ogden, A.; Aneja, R.; Zhou, J. Microtubule-Binding Proteins as Promising Biomarkers of Paclitaxel Sensitivity in Cancer Chemotherapy. Med. Res. Rev. 2016, 36, 300-312.
94. Cao, Y. N.; Zheng, L. L.; Wang, D.; Liang, X. X.; Gao, F.; Zhou, X. L. Recent advances in microtubule-stabilizing agents. Eur. J. Med. Chem. 2018, 143, 806-828.
95. Li, Y.; Zhou, W.; Tang, K.; Chen, X.; Feng, Z.; Chen, J. Silencing Aurora-A leads to re-sensitization of breast cancer cells to Taxol through downregulation of SRC-mediated ERK and mTOR pathways. Oncol. Rep. 2017, 38, 2011-2022.
96. Li, Y.; Tang, K.; Zhang, H.; Zhang, Y.; Zhou, W.; Chen, X. Function of Aurora kinase A in Taxol-resistant breast cancer and its correlation with P-gp. Mol. Med. Rep. 2011, 4, 739-746.

97. Habu, T.; Matsumoto, T. p31(comet) inactivates the chemically induced Mad2-dependent spindle assembly checkpoint and leads to resistance to anti-mitotic drugs. Springerplus 2013, 2, 562.

98. Marcus, A. I.; Peters, U.; Thomas, S. L.; Garrett, S.; Zelnak, A.; Kapoor, T. M.; Giannakakou, P. Mitotic kinesin inhibitors induce mitotic arrest and cell death in Taxol-resistant and -sensitive cancer cells. J. Biol. Chem. 2005, 280, 11569-11577.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of downregulating the expression of at least one gene in a patient in need thereof comprising:
administering to the patient in need thereof a therapeutically effective amount of a composition comprising Formula (I)

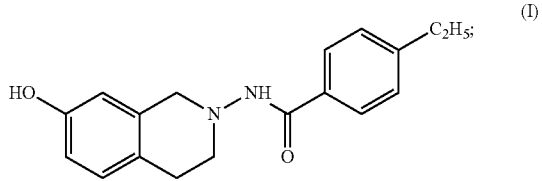 [SMILES: CCc1ccc(C(=O)NN2CCc3ccc(O)cc3C2)cc1]

and a pharmaceutically acceptable carrier;
wherein the at least one gene is selected from the group consisting of amphiregulin (AREG), epiregulin (EREG), inhibitor of DNA binding 1 (ID1), inhibitor of DNA binding 3 (ID3), inhibitor of DNA binding 4 (ID4), killer cell lectin like receptor C3 (KLRC3), cyclooxygenase-2 (COX2), and intercellular adhesion molecule 1 (ICAM-1).

2. The method of claim 1, wherein the patient has breast cancer.

3. The method of claim 2, wherein the breast cancer is triple negative breast cancer (TNBC).

4. The method of claim 1, wherein expression of amphiregulin (AREG) and epiregulin (EREG) are downregulated.

5. The method of claim 1, wherein expression of inhibitor of DNA binding 1 (ID1), inhibitor of DNA binding 3 (ID3), and inhibitor of DNA binding 4 (ID4) are downregulated.

6. The method of claim 1, wherein the expression of killer cell lectin like receptor C3 (KLRC3) is downregulated.

7. The method of claim 1, wherein expression of cyclooxygenase-2 (COX2) is downregulated.

8. The method of claim 1, wherein expression of intercellular adhesion molecule 1 (ICAM-1) is downregulated.

9. A method of downregulating oncostatin M(OSM) signaling in a patient having at least one tumor cell comprising:
administering to the patient a therapeutically effective amount of a compound comprising Formula (I)

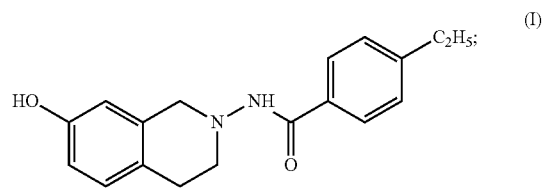 [SMILES: CCc1ccc(C(=O)NN2CCc3ccc(O)cc3C2)cc1]

wherein administration of the compound to the patient downregulates oncostatin M(OSM) signaling.

10. The method of claim 9, wherein the at least one tumor cell is a breast cancer cell.

11. The method of claim 10, wherein the breast cancer cell is a triple negative breast cancer (TNBC) cell.

12. The method of claim 9, wherein expression of amphiregulin (AREG) and epiregulin (EREG) are downregulated.

13. The method of claim 9, wherein expression of inhibitor of DNA binding 1 (ID1), inhibitor of DNA binding 3 (ID3), and inhibitor of DNA binding 4 (ID4) are downregulated.

14. The method of claim 9, wherein the expression of killer cell lectin like receptor C3 (KLRC3) is downregulated.

15. The method of claim 9, wherein expression of cyclooxygenase-2 (COX2) is downregulated.

16. The method of claim 9, wherein expression of intercellular adhesion molecule 1 (ICAM-1) is downregulated.

* * * * *